(12) United States Patent
Sterzycki et al.

(10) Patent No.: US 6,265,394 B1
(45) Date of Patent: Jul. 24, 2001

(54) BIS QUATERNARY MRSA CEPHEM DERIVATIVES

(75) Inventors: Roman Z. Sterzycki, Madison; Oak K. Kim, Guilford; Yasutsugu Ueda, Clinton; Stanley V. D'Andrea, Middletown; Dane M. Springer, North Haven, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/366,854

(22) Filed: Aug. 4, 1999

Related U.S. Application Data

(63) Continuation-in-part of application No. 09/298,243, filed on Apr. 23, 1999, now abandoned, which is a continuation of application No. 09/114,808, filed on Jul. 13, 1998, now abandoned.
(60) Provisional application No. 60/061,002, filed on Jul. 31, 1997.

(51) Int. Cl.$^7$ ...................... A61K 31/545; C07D 501/36; A61P 31/04
(52) U.S. Cl. .......................... 514/203; 540/224; 540/225
(58) Field of Search ..................................... 540/224, 225; 514/203

(56) References Cited

U.S. PATENT DOCUMENTS

| | | | |
|---|---|---|---|
| 5,559,108 | 9/1996 | Kim et al. | 514/210 |
| 5,567,698 | 10/1996 | Kim et al. | 514/210 |
| 5,620,969 | * 4/1997 | Bronson | 540/225 |
| 5,734,047 | * 3/1998 | Kim | 540/224 |
| 6,093,712 | * 7/2000 | Matiskella | 540/224 |

FOREIGN PATENT DOCUMENTS

| | | |
|---|---|---|
| 209751A2 | 1/1987 | (EP) . |
| 264091A2 | 4/1988 | (EP) . |
| 700916A1 | 3/1996 | (EP) . |
| WO96/02548A1 | 2/1996 | (WO) . |
| WO97/37997 | 10/1997 | (WO) . |
| 98/23621 | * 6/1998 | (WO) . |

OTHER PUBLICATIONS

I. E. El–Kholy, et al, "Action of Amines and Carbonyl Reagents on 3,5–Diphenyl–4–Pyrone and Its Thio Analogue," J. Heterocyclic Chem., 11, pp. 487–490, 1974.

* cited by examiner

*Primary Examiner*—Mark L. Berch
(74) *Attorney, Agent, or Firm*—David M. Morse

(57) ABSTRACT

Provided by the present invention are cephem derivatives represented by the general formula

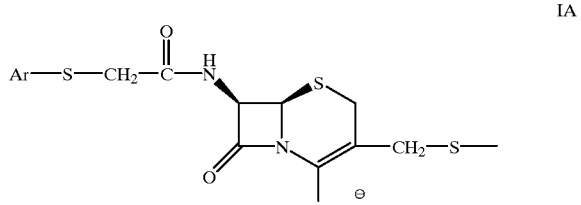

IA

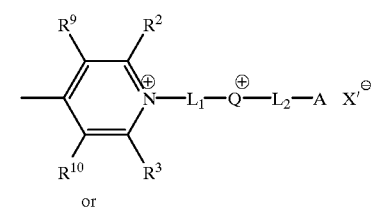

or

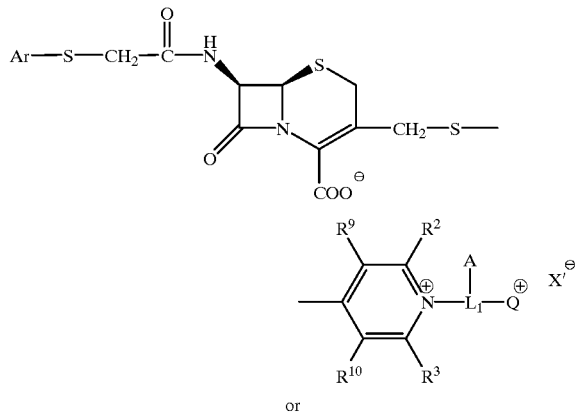

IB or

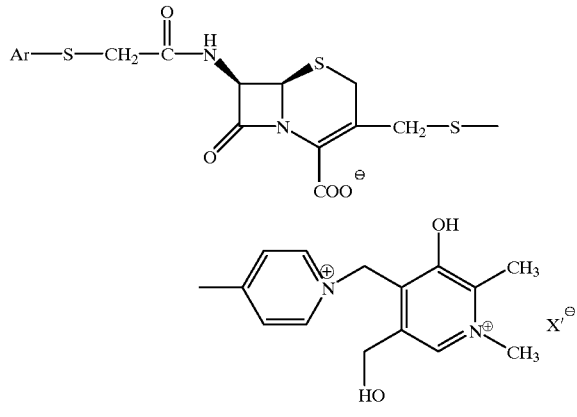

IC and

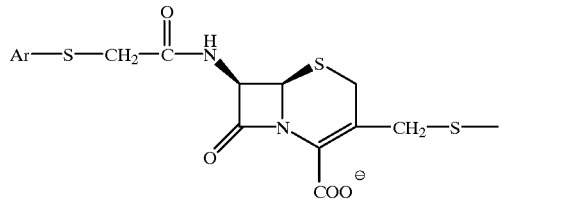

ID

-continued

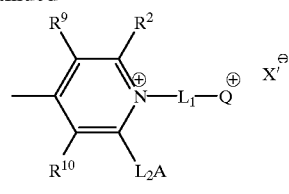

wherein Ar is an optionally substituted lipophilic phenyl, naphthyl or pyridyl group; $L_1$ and $L_2$ are $(C_1-C_6)$alkylene optionally substituted with hydroxy or oxo and/or optionally interrupted with a vinylene group, S, O, aryl, heteroaryl,

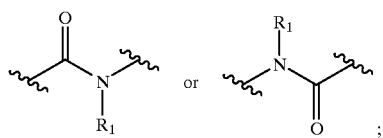

in which $R_1$ is H or $(C_1-C_6)$alkyl; A is $CO_2H$, $PO_3H$, $SO_3H$, tetrazolyl or

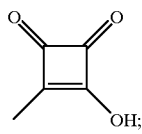

$X^\ominus$ is a pharmaceutically acceptable anion; and Q is an quaternized nitrogen group. The derivatives are gram-positive antibacterial agents especially useful in the treatment of diseases caused by methicillin-resistant *Staphylococcus aureus*.

22 Claims, No Drawings

BIS QUATERNARY MRSA CEPHEM DERIVATIVES

CROSS-REFERENCE TO RELATED APPLICATIONS

This is a continuation-in-part of our co-pending application Ser. No. 09/298,243 filed Apr. 23, 1999 abandoned which in turn is a continuation of application Ser. No. 09/114,808 filed Jul. 13, 1998, now abandoned, which claims the priority of provisional application Serial No. 60/061,002 filed Jul. 31, 1997.

BACKGROUND OF THE INVENTION

1. Field of the Invention

The present invention is directed to new cephem derivatives represented by the general formula

IA

IB

IC

ID wherein Ar is an optionally substituted lipophilic phenyl, naphthyl or pyridyl group; $L_1$ and $L_2$ are $(C_1-C_6)$alkylene optionally substituted with hydroxy or oxo and/or optionally interrupted with a vinylene group, S, O, aryl or heteroaryl, or a group of the formula or wherein $R^1$ is hydrogen or $(C_1-C_6)$alkyl or can optionally contain A; A is $CO_2H$, $PO_3H$, $SO_3H$, tetrazolyl, or $R^2$, $R^3$, $R^9$ and $R^{10}$ are hydrogen or optionally substituted $(C_1-C_6)$alkyl, $x'^{\ominus}$ is a pharmaceutically acceptable anion; and Q is a quaternized nitrogen group. The derivatives IA, IB, IC and ID, including pharmaceutically acceptable salts and prodrugs thereof, are gram-positive antibacterial agents especially useful in the treatment of diseases caused by methicillin-resistant *Staphylococcus aureus* (also referred to below as MRSA or methicillin-resistant *S. aureus*).

2. Description of the Prior Art

The literature discloses a vast number of cephem derivatives having a wide variety of C-3 and C-7 substituents.

Cephems having at the 3-position substituents containing two quaternary nitrogens plus an acidic group, —$CO_2H$ or —$SO_3H$, are disclosed in EP 700,916 and EP 264,091. Such publications, however, disclose compounds with different 7-substituents than in applicants' compounds and the 3-substituents are of the type

—CH=CHCH$_2$— and

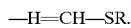

Cephems containing two quaternary nitrogens in the C-3 substituent are disclosed in WO 96/02548, but here again the C-7 substituents differ from those in applicants' compounds and the C-3 substituents are of the type U.S. Pat. No. 5,567,698 discloses cephems of the formula

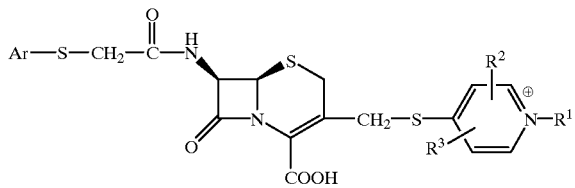

wherein Ar is an aryl group selected from

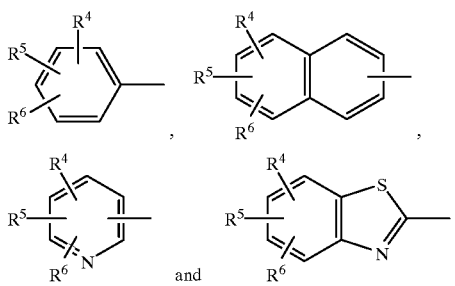

in which $R^4$, $R^5$ and $R^6$ are each independently hydrogen, halogen, trihalomethyl, nitro, $C_1$–$C_6$ alkyl, —$(CH_2)_nOR^7$ or —$(CH_2)_nSR^7$; n is an integer of from 1 to 6; $R^7$ is hydrogen or $C_1$–$C_6$ alkyl; $R^1$ is —$CR^8R^9R^{10}$, —$(CH_2)_nCONR^8R^9$ and —$(CH_2)_nCOR^8$ in which $R^8$, $R^9$ and $R^{10}$ are each independently hydrogen, substituted or unsubstituted $C_1$–$C_{15}$ alkyl, $C_2$–$C_{15}$ alkenyl or $C_2$–$C_{15}$ alkynyl, substituted or unsubstituted phenyl, phenyl($C_1$–$C_6$)alkyl, naphthyl or naphthyl ($C_1$–$C_6$)alkyl or a sugar moiety of the formula

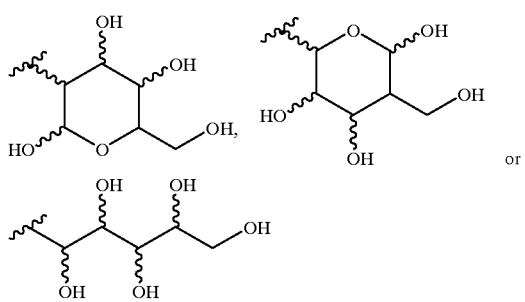

in which said alkyl, alkenyl or alkynyl group, or the alkyl portion of the said phenyl($C_1$–$C_6$)alkyl or naphthyl($C_1$–$C_6$) alkyl group can be substituted by one or more hydroxy groups and said phenyl or naphthyl group, or the phenyl or naphthyl portion of said phenyl ($C_1$–$C_6$)alkyl or naphthyl ($C_1$–$C_6$)alkyl group can be substituted by one or more hydroxy, $C_1$–$C_6$ alkyl, $C_1$–$C_6$ alkoxy, halo or halo($C_1$–$C_6$) alkyl groups; n is as defined above; $R^2$ and $R^3$ are each independently hydrogen, $C_1$–$C_6$ alkyl, or amino($C_1$–$C_6$) alkylcarbonyl-amino; and $R^{11}$ is hydrogen, an anionic charge or a carboxyl-protecting group provided that when $R^{11}$ is hydrogen or a protecting group, there is also a counter ion; or a pharmaceutically acceptable salt or prodrug thereof.

U.S. Pat. No. 5,559,108 discloses cephem compounds of the formula

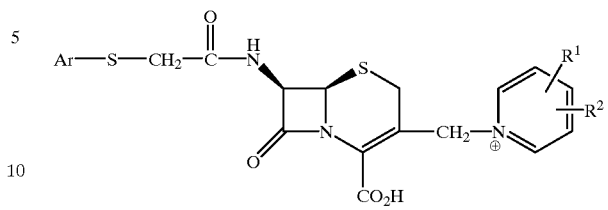

wherein Ar is an aryl group selected from the group consisting of

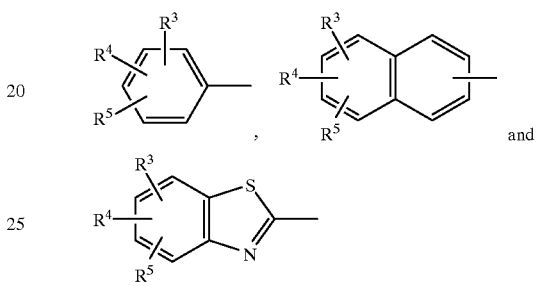

in which $R^3$, $R^4$ and $R^5$ are each independently hydrogen, halogen, trihalomethyl, $C_1$–$C_6$ alkyl, —$(CH_2)_nOR^6$ or —$(CH_2)_nSR^6$, with the proviso that when Ar is a phenyl group, $R^3$, $R^4$ and $R^5$ may not all be hydrogen; n is an integer of from 1 to 6; $R^6$ is hydrogen or $C_1$–$C_6$ alkyl; $R^1$ and $R^2$ are each independently hydrogen, —$(CH_2)_mCONR^7R^8$, —$(CH_2)_mCOR^7$, —$(CH_2)_mCO_2R^7$, —$(CH_2)_mCN$, —$(CH^2)_m NR^7R^8$, —$(CH_2)_mOR^7$, —$(CH_2)_mNHCONR^7R^8$ or —$(CH_2)_mNHCOR^7$ in which m is 0 or an integer of from 1 to 6 and $R^7$ and $R^8$ are each independently hydrogen, $C_1$–$C_6$ alkyl substituted by one or two amino or hydroxyl groups or a group of the formula

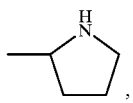

or $R^7$ and $R^8$ taken together with the nitrogen atom to which they are attached represent

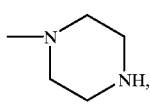

with the proviso that $R^1$ and $R^2$ may not both be hydrogen; and $R^9$ is hydrogen, an anionic charge or a carboxyl-protecting group, provided that when $R^9$ is hydrogen or a protecting group, there is also present a ounter ion; or a pharmaceutically acceptable salt thereof.

In co-pending application Ser. No. 08/829,126 filed Mar. 28, 1997, there are disclosed cephem derivatives of the formula

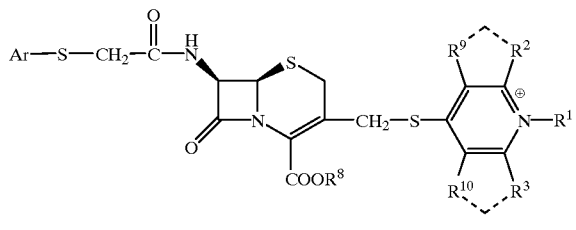

wherein Ar is a group of the formula

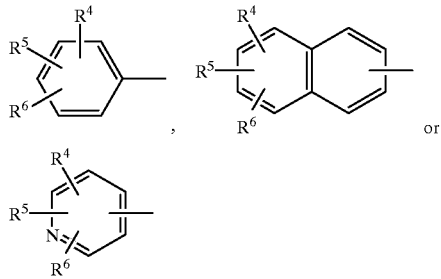

in which $R^4$, $R^5$ and $R^6$ are each independently hydrogen, halogen, trihalomethyl, nitro, amino, hydroxy, hydroxy ($C_1$–$C_6$)alkyl, ($C_1$–$C_6$)alkyl, —$(CH_2)_nOR^7$ or —$(CH_2)_n SR^7$; n is an integer of from 1 to 6; $R^7$ is hydrogen or($C_1$–$C_6$)alkyl; $R^1$ represents alkyl having from 1 to 10 carbons or cycloalkyl having from 3 to 6 carbons, said alkyl or cycloalkyl group being linked by a carbon atom to the quaternary nitrogen and having a carboxy, —$SO_3H$ or tetrazolyl substituent, and said alkyl group being optionally interrupted by —S— or

and optionally substituted by one or more of ($C_1$–$C_6$) alkylthio, hydroxy, ($C_1$–$C_6$)alkylsulfinyl, ($C_1$–$C_6$) alkylsulfonyl, carbamoyl, ureido, $C_2$–$C_6$ alkenyl, halo, oxo, hydroxyimino, heteroaryl or phenyl in which the phenyl or heteroaryl group is optionally substituted by up to three hydroxy or ($C_1$–$C_6$)alkoxy groups; $R^7$ is as defined above; $R^2$, $R^3$, $R^9$ and $R^{10}$ are each independently hydrogen, ($C_1$–$C_{10}$)alkyl or ($C_1$–$C_{10}$)alkyl substituted by one or more, preferably one or two, substituents independently selected from $CO_2H$, hydroxy and $NR^{11}R^{12}$ in which $R^{11}$ and $R^{12}$ are each independently hydrogen or ($C_1$–$C_6$)alkyl, and $R^2$ and $R^9$ or $R^3$ and $R^{10}$ can optionally be joined in a ring, preferably a 5–6 membered ring; and $R^8$ is hydrogen or a protecting group; or a pharmaceutically acceptable salt or prodrug thereof.

SUMMARY OF THE INVENTION

In one aspect the present invention provides a novel series of cephem derivatives of the general formula

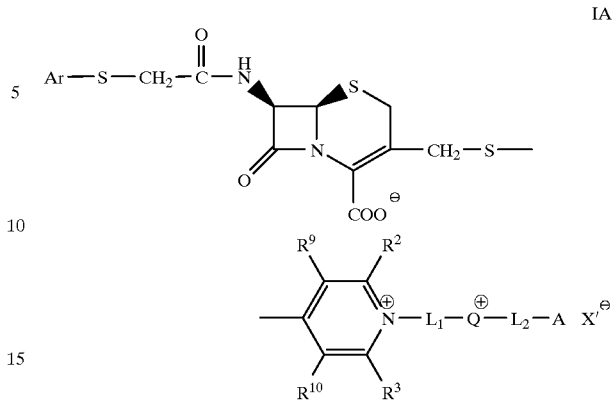

wherein Ar is a group of the formula

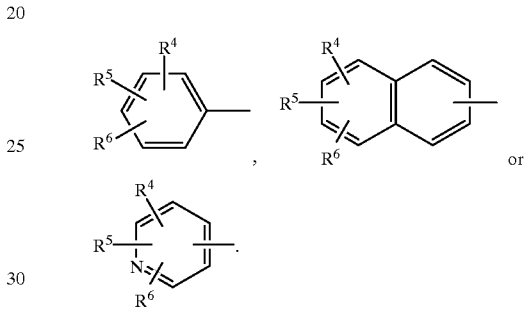

$R^4$, $R^5$ and $R^6$ are each independently hydrogen, halogen, trihalomethyl, nitro, amino, hydroxy, hydroxy($C_1$–$C_6$)alkyl, ($C_1$–$C_6$)alkyl, —$(CH_2)_nOR^7$ or —$(CH_2)_nSR^7$; n is an integer of from 1 to 6; $R^7$ is hydrogen or ($C_1$–$C_6$)alkyl; $L_1$ and $L_2$ are each independently ($C_1$–$C_6$)alkylene optionally substituted with hydroxy or oxo and/or optionally interrupted with a vinylene group, S, O, an aryl or heteroaryl residue, or

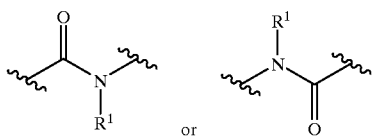

wherein $R^1$ is H or $C_1$–$C_6$ alkyl; A is $CO_2H$, $PO_3H$, $SO_3H$, tetrazolyl or

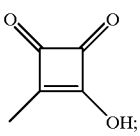

Q is selected from the group consisting of:

(1)

wherein $R^{14}$ and $R^{15}$ are each independently ($C_1$–$C_{10}$)alkyl optionally substituted with OH or $C(O)NH_2$;

(2)

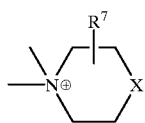

wherein X is $CH_2$, O, S, SO or $SO_2$;
R$^7$ is H, ($C_1$–$C_6$) alkyl, ($C_3$–$C_6$)cycloalkyl, OH, $CONH_2$, aryl or heteroaryl and can be located anywhere on the ring including X when X is $CH_2$;

(3)

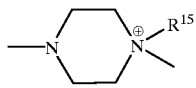

wherein R$^{15}$ is ($C_1$–$C_6$)alkyl or ($C_3$–$C_6$)cycloalkyl optionally substituted with OH or $CONH_2$, or R$^{15}$ is aryl or heteroaryl;

(4)

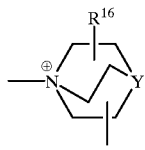

wherein Y is CH or N and R$^{16}$ is as defined above for R$^7$;

(5)

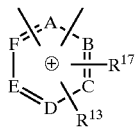

wherein A through F can be CH or N, and either 1 or 2 of the non-adjacent atoms being N with the remainder being CH, exactly one N being quaternized by attachment to $L_1$, $L_2$, R$^{17}$, or R$^{13}$; R$^{13}$ and R$^{17}$ are as defined above for R$^7$;

(6)

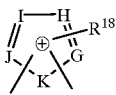

wherein G, H, I, and J are either CH or N, K is either $CH_2$, NH, or S, either 1, 2, or 3 of the ring atoms being nitrogen with the remainder being $CH_2$, exactly one nitrogen being quaternized by $L_1$, $L_2$, or R$^{18}$; and R$^{18}$ is as defined above for R$^7$; R$^2$, R$^3$, R$^9$ and R$^{10}$ are each independently hydrogen, ($C_1$–$C_{10}$)alkyl or ($C_1$–$C_{10}$)alkyl substituted by one or more substituents independently selected from hydroxy and NR$^{11}$R$^{12}$ in which R$^{11}$ and R$^{12}$ are each independently hydrogen or ($C_1$–$C_6$)alkyl, and x'$^{\ominus}$ is a pharmaceutically acceptable anion; or a pharmaceutically acceptable salt or prodrug thereof.

In another aspect the present invention provides a novel series of cephem derivatives of the general formula

IB

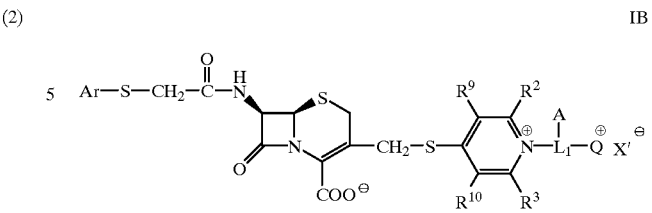

wherein Ar is a group of the formula

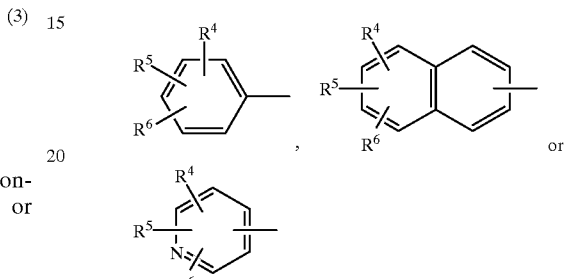

R$^4$, R$^5$ and R$^6$ are each independently hydrogen, halogen, trihalomethyl, nitro, amino, hydroxy, hydroxy($C_1$–$C_6$)alkyl, ($C_1$–$C_6$)alkyl, —$(CH_2)_n$OR$^7$ or —$(CH_2)_n$SR$^7$; n is an integer of from 1 to 6; R$^7$ is hydrogen or ($C_1$–$C_6$)alkyl; $L_1$ is ($C_1$–$C_6$)alkylene optionally substituted with hydroxy or oxo and/or optionally interrupted with a vinylene group, S, O, an aryl or heteroaryl residue or

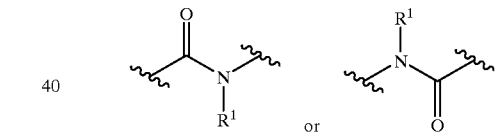

wherein R$^1$ is H or ($C_1$–$C_6$)alkyl; A is $CO_2H$, $PO_3H$, $SO_3H$, tetrazolyl or

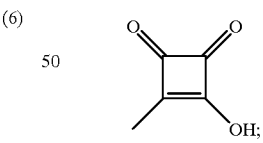

Q is selected from the group consisting of:

(1)

wherein R$^{14}$, R$^{15}$ and R$^{16}$ are each independently ($C_1$–$C_{10}$) alkyl optionally substituted with OH or C(O)NH$_2$;

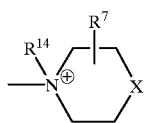
(2)

wherein X is $CH_2$, O, S, SO or $SO_2$;
$R^7$ is H, $(C_1-C_6)$ alkyl, $(C_3-C_6)$cycloalkyl, OH, $CONH_2$, aryl or heteroaryl and can be located anywhere on the ring including X when X is $CH_2$ and $R^{14}$ is as defined above;

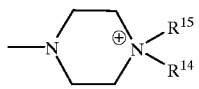
(3)

wherein $R^{15}$ is $(C_1-C_6)$alkyl or $(C_3-C_6)$cycloalkyl optionally substituted with OH or $CONH_2$, or $R^{15}$ is aryl or heteroaryl; and $R^{14}$ is as defined above;

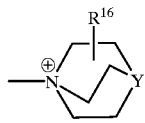
(4)

wherein Y is CH or N and $R^{16}$ is as defined above for $R^7$;

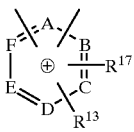
(5)

wherein A through F can be CH or N, either 1 or 2 of the non-adjacent atoms being N with the remainder being CH, one N being quaternized by attachment to $L_1$, $L_2$, $R^{17}$, or $R^{13}$; $R^{13}$ and $R^{17}$ are as defined for $R^7$;

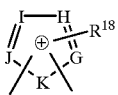
(6)

wherein G, H, I, and J are either CH or N, K is either $CH_2$, NH, or S, either 1, 2, or 3 of the ring atoms being nitrogen with the remainder being $CH_2$, exactly one nitrogen being quaternized by $L_1$, $L_2$, or $R^{18}$; and $R^{18}$ is as defined above for $R^7$;
$R^2$, $R^3$, $R^9$ and $R^{10}$ are each independently hydrogen, $(C_1-C_{10})$alkyl or $C_1-C_{10}$)alkyl substituted by one or more substituents independently elected from hydroxy and $NR^{11}R^{12}$ in which $R^{11}$ and $R^{12}$ are each independently hydrogen or $(C_1-C_6)$alkyl, and $x'^{\ominus}$ is a pharmaceutically acceptable anion; or a pharmaceutically acceptable salt or prodrug thereof.

In yet another aspect the present invention provides a novel series of cephem derivatives of the general formula

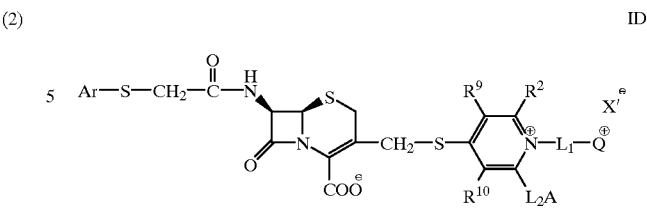
ID wherein Ar is a group of the formula

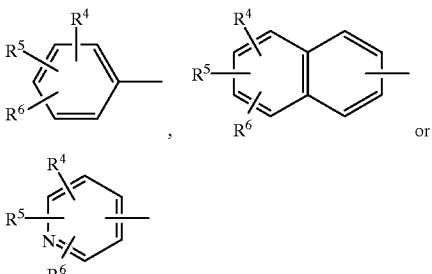

$R^4$, $R^5$ and $R^6$ are each independently hydrogen, halogen, trihalomethyl, nitro, amino, hydroxy, hydroxy$(C_1-C_6)$alkyl, $(C_1-C_6)$alkyl, $-(CH_2)_nOR^7$ or $-(CH_2)_nSR^7$; n is an integer of from 1 to 6; $R^7$ is hydrogen or $(C_1-C_6)$alkyl; $L_1$ is $(C_1-C_6)$alkylene optionally substituted with hydroxy or oxo and/or optionally interrupted with a vinylene group, S, O, aryl or heteroaryl, or

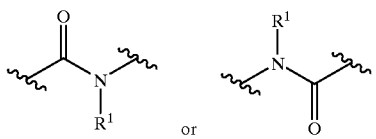

wherein $R^1$ is H or $(C_1-C_6)$alkyl; A is $CO_2H$, $PO_3H$, $SO_3H$, tetrazolyl or

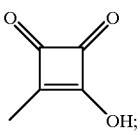

Q is selected from the group consisting of:

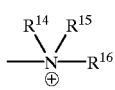
(1)

wherein $R^{14}$, $R^{15}$ and $R^{16}$ are each independently $(C_1-C_{10})$ alkyl optionally substituted with OH or $C(O)NH_2$;

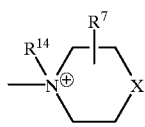
(2)

wherein X is $CH_2$, O, S, SO or $SO_2$; $R^7$ is H, $(C_1-C_6$ alkyl), $(C_3-C_6)$cycloalkyl, OH, $CONH_2$, aryl or heteroaryl and can be located anywhere on the ring including X when X is $CH_2$; and $R^{14}$ is as defined above;

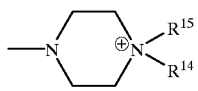
(3)

wherein $R^{15}$ is $(C_1-C_6)$alkyl or $(C_3-C_6)$cycloalkyl optionally substituted with OH or $CONH_2$, or $R^{15}$ is aryl or heteroaryl; and $R^{14}$ is as defined above;

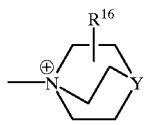
(4)

wherein Y is CH or N and $R^{16}$ is as defined above for $R^7$;

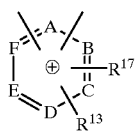
(5)

wherein A through F can be CH or N, and either 1 or 2 of the non-adjacent atoms being N with the remainder being CH, one N being quaternized by attachment to $L_1$, $L_2$, $R^{17}$, or $R^{13}$; $R^{13}$ and $R^{17}$ are as defined for $R^7$;

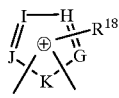
(6)

wherein G, H, I, and J are either CH or N, K is either $CH_2$, NH, or S, either 1, 2, or 3 of the ring atoms being nitrogen with the remainder being $CH_2$, one nitrogen being quaternized by $L_1$, $L_2$, or $R^{18}$; and $R^{18}$ is as defined above for $R^7$; $R^2$, $R^9$ and $R^{10}$ are each independently hydrogen, $(C_1-C_{10})$ alkyl or $(C_1-C_{10})$alkyl substituted by one or more substituents independently selected from hydroxy and $NR^{11}R^{12}$ in which $R^{11}$ and $R^{12}$ are each independently hydrogen or $(C_1-C_6)$alkyl, and $x'^{\ominus}$ is a pharmaceutically acceptable anion; or a pharmaceutically acceptable salt or prodrug thereof.

In a last aspect, the present invention provides a novel series of cephem derivatives of the general formula

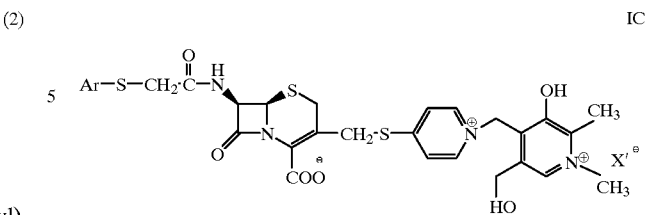
IC wherein Ar is a group of the formula

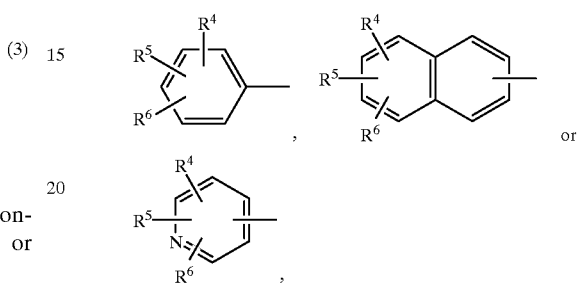

$R^4$, $R^5$ and $R^6$ are each independently hydrogen, halogen, trihalomethyl, nitro, amino, hydroxy, hydroxy$(C_1-C_6)$alkyl, $(C_1-C_6)$alkyl, $-(CH_2)_nOR^7$ or $-(CH_2)_nSR^7$; n is an integer of from 1 to 6; $R^7$ is hydrogen or $(C_1-C_6)$alkyl; and $x'^{\ominus}$ is a pharmaceutically acceptable anion; or a pharmaceutically acceptable salt or prodrug thereof.

The compounds of formulae IA, IB, IC and ID are antibacterial agents useful in the treatment of infections in humans and other animals caused by a variety of gram-positive bacteria, particularly methicillin-resistant S. aureus.

Also included within the scope of the present invention are processes for preparing the compounds of formulae IA, IB, IC and ID and pharmaceutical compositions containing said compounds in combination with pharmaceutically acceptable carriers or excipients.

DETAILED DESCRIPTION

The present invention provides cephem derivatives of general formula IA, IB, IC and ID above which are antibacterial agents useful in the treatment of infectious diseases in humans and other animals. The compounds exhibit good activity against a wide variety of gram-positive microorganisms, e.g. S. pneumoniae, S. pyogenes, S. aureus, E. faecalis, S. epidermis and S. hemolyticus and are particularly useful against strains of methicillin-resistant S. aureus.

The compounds of the present invention are characterized by a combination of a lipophilic 7-substitutent of the type

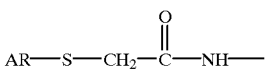

wherein Ar is an aromatic group selected from optionally substituted phenyl, naphthyl or pyridyl and a 3-substituent of the type

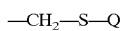

where Q contains two quaternary nitrogen atoms and an acidic functional group selected from $CO_2H$, $PO_3H$, $SO_3H$, tetrazolyl or

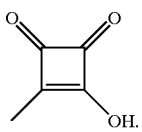

To elaborate on the definitions for the substituents of the formula I compounds:

(a) "Halogen" includes chloro, bromo, fluoro and iodo and is preferably chloro or bromo;

(b) "Trihalomethyl" includes trichloromethyl, trifluoromethyl, tribromomethyl and triiodomethyl, but is preferably trifluoromethyl;

(c) The term "alkyl" refers to a straight or branched chain monovalent alkane having the specified number of carbon atoms, e.g. in the case of ($C_1$–$C_6$)alkyl, the alkyl group may have from 1 to 6 carbon atoms.

(d) The term "aryl" or "aryl residue" refers to aromatic carbocyclic containing from 6 to 22 atoms. An aryl group can contain at least one ring having at least six carbons with up to five such rings being present containing up to 22 carbons. Preferred aryl groups are phenyl, naphthyl and phenanthrenyl with phenyl and naphthyl being most preferred.

(e) The term "heteroaryl" or "heteroaryl residue" refers to a monocyclic aromatic ring having 5 or 6 ring atoms, or a bicyclic aromatic ring having 8 to 10 ring atoms containing at least one heteroatom selected from O, S or N. Examples of heteroaryl include thiazolyl, imidazolyl, pyridyl, pyrrolyl, oxazolyl, isoxazolyl, isothiazolyl, oxadiazolyl, thiadiazolyl, triazolyl and tetrazolyl.

(f) "Oxo" refers to

and (g) "Vinylene" refers to $CH_2$=CH—.

The term "pharmaceutically acceptable salt" as used herein is intended to include the nontoxic acid addition slats with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Some of the compounds of the present invention have an acidic hydrogen and can, therefore, be converted with bases in a conventional manner into pharmaceutically acceptable salts. Such salts, e.g. ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine, are also intended to be encompassed by the term "pharmaceutically acceptable salt".

Also encompassed by the present invention are compounds of the above formulae where the carboxylic acid group is protected by a readily removable ester groups which have been employed to block a carboxyl group during the reaction steps used to prepare compounds I and which can be removed by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation, etc. Examples of such protecting groups include benzhydryl, p-nitrobenzyl, 2-naphthylmethyl, allyl, benzyl, p-methoxybenzyl, trichloroethyl, silyl such as trimethylsilyl, phenacyl, acetonyl, o-nitrobenzyl, 4-pyridylmethyl and ($C_1$–$C_6$)alkyl such as methyl, ethyl or t-butyl. Included within such protecting groups are those which are hydrolyzed under physiological conditions such as pivaloyloxymethyl, acetoxymethyl, phthalidyl, indanyl, α-acetoxyethyl, α-pivaloyloxyethyl, and methoxymethyl. Compounds of formula I with such physiologically hydrolyzable carboxyl protecting groups are also referred to herein and in the claims as "prodrugs". Compounds of formula I containing a physiologically removable protecting group are useful directly as antibacterial agents. Compounds where a carboxyl-protecting group is not physiologically removable are useful intermediates which can be easily converted to the active form by conventional deblocking procedures well-known to those skilled in the art.

Compounds of formula I wherein a hydroxyl substituent is esterified with a group hydrolyzable under physiological conditions are also included within the scope of the term "prodrug" as used herein and in the claims. Such hydroxyl protecting groups may be employed, for example, to further increase the aqueous solubility of a formula I compound. Illustrative of suitable ester "prodrugs" of this type are compounds of forula I wherein one or more hydroxy substituent groups are converted to sulfate (—$OSO_3H$) or phosphate (—$OPO_3H_2$) groups.

A preferred embodiment of the present invention comprises compounds of the formula

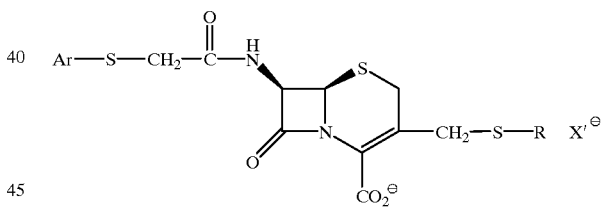

wherein Ar is

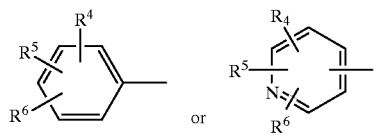

in which $R^4$, Rs and $R^6$ are each independently hydrogen, halogen, ($C_1$–$C_6$)alkyl, trifluoromethyl, hydroxy, hydroxy ($C_1$–$C_6$)alkyl or amino and R is

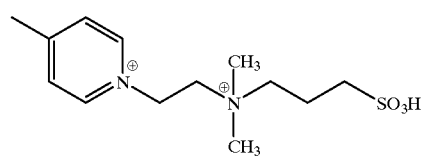

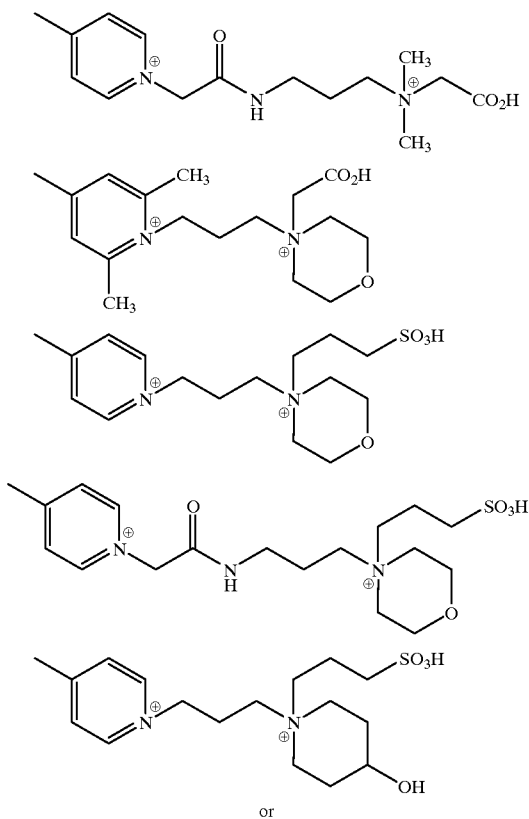
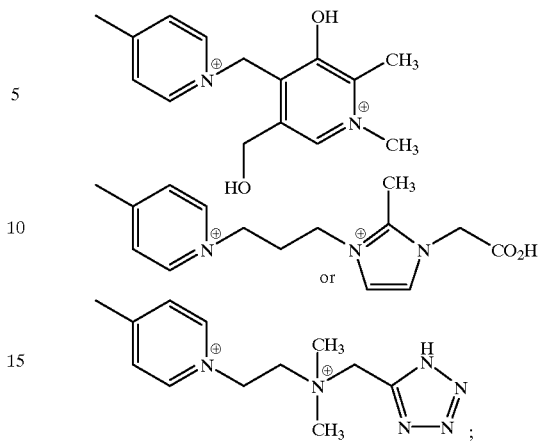
and pharmaceutically acceptable salts and prodrugs thereof.
Another preferred embodiment of the present invention comprises the compounds mentioned directly above where Ar is
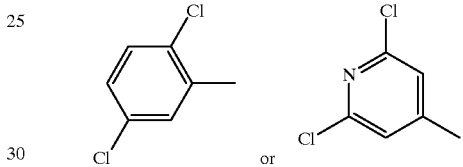
Another preferred embodiment of the present invention comprises the compounds:
(Example 1)
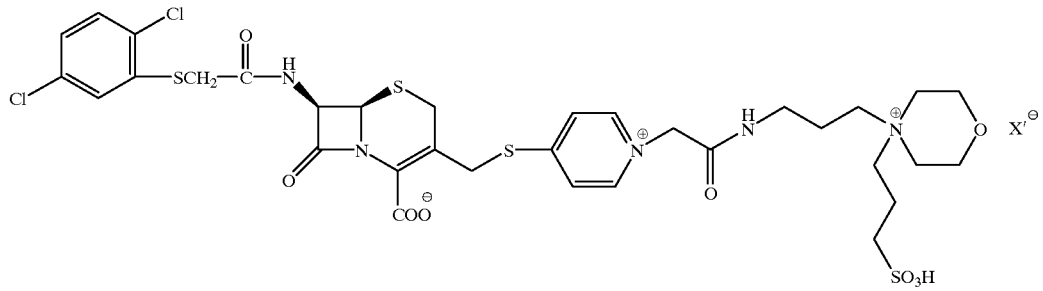
(Example 2)
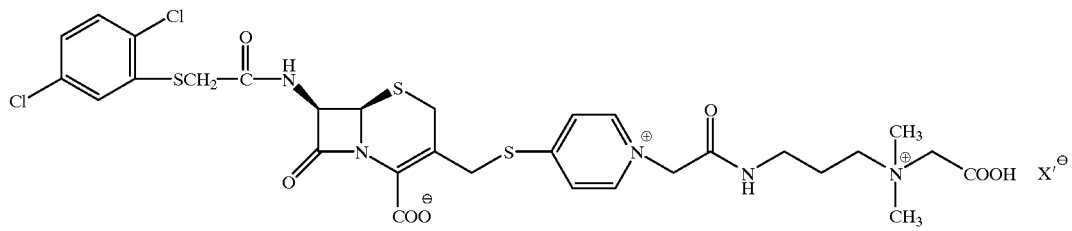

-continued
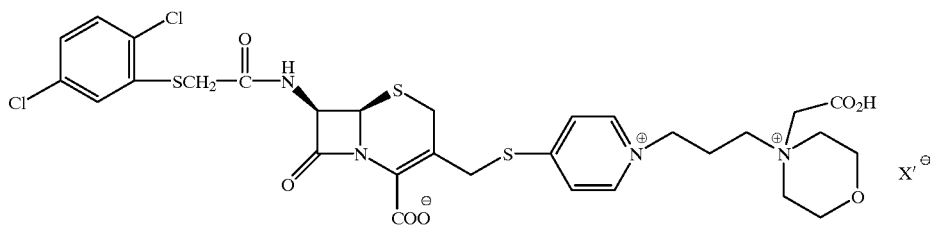
(Example 3)
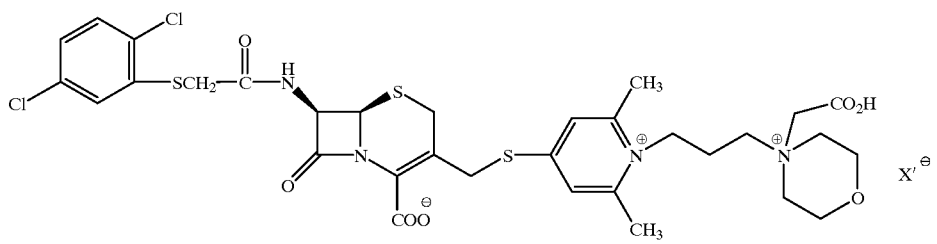
(Example 4)
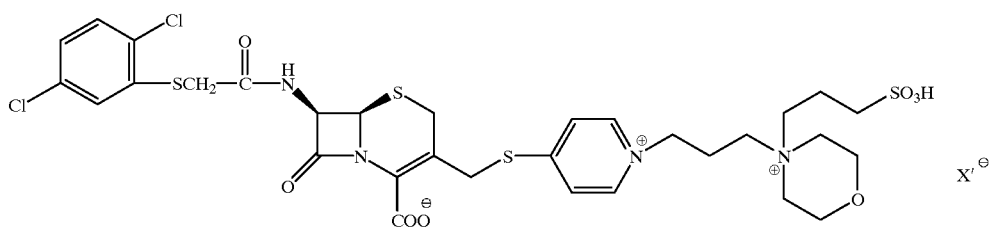
(Example 5)
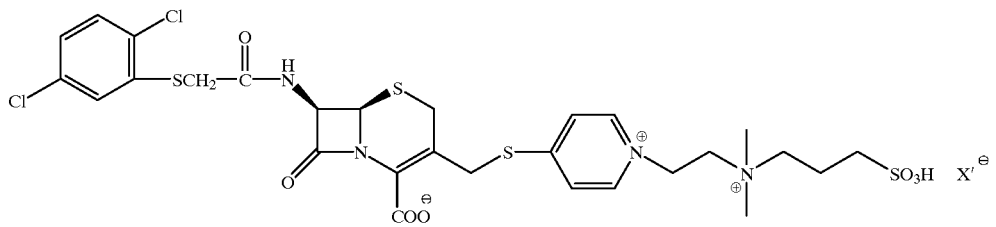
(Example 6)
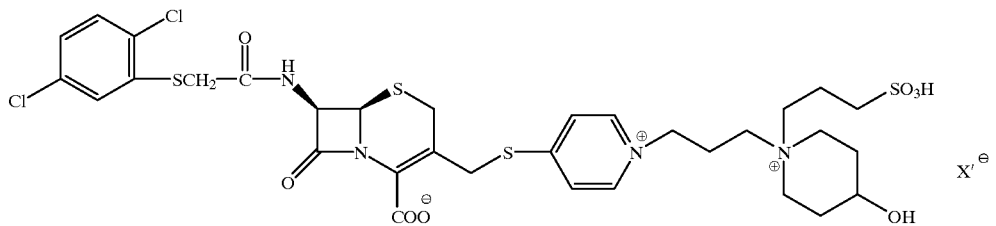
(Example 7)
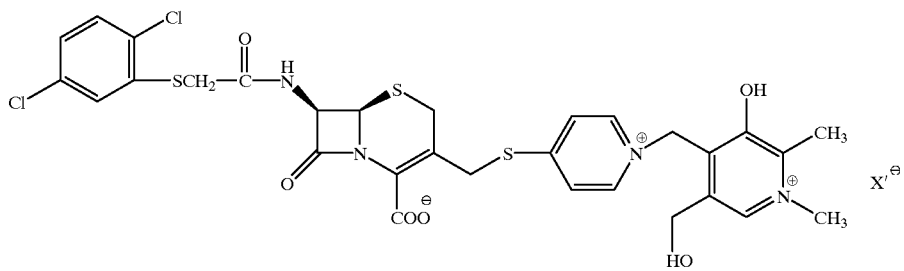
(Example 8)

(Example 9)

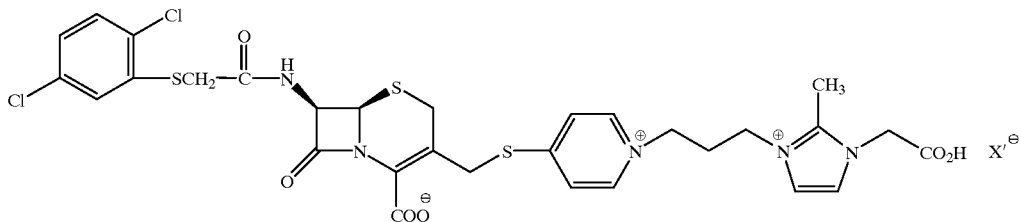

(Example 10)

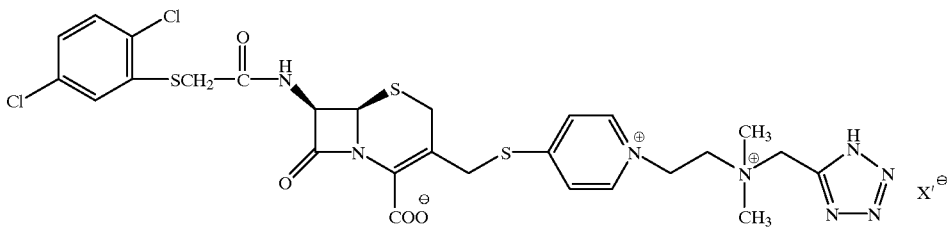

X'⊖ is a pharmaceutically acceptable anion such as Cl, Br, I, etc.

The compounds of the present invention can be made by conventional methods. A suitable procedure is summarized by the following reaction scheme:

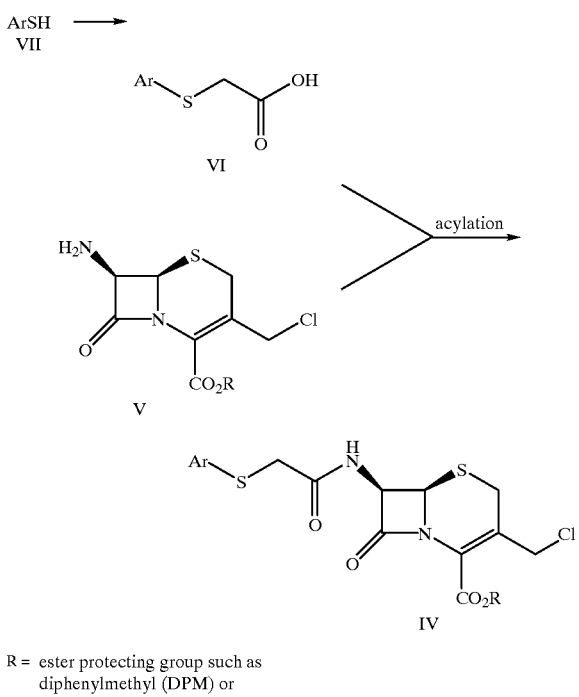

R = ester protecting group such as diphenylmethyl (DPM) or para-methoxybenzyl (PMB)

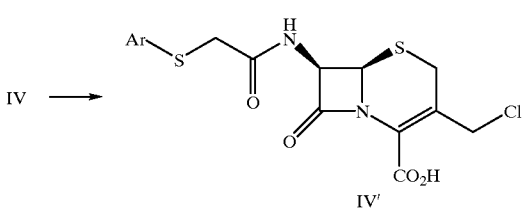

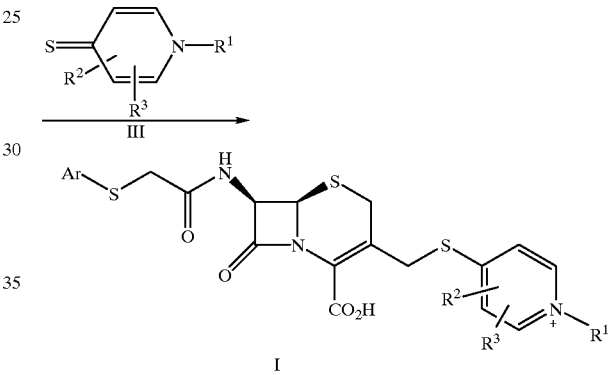

To elaborate on the above process, thiol VII is converted into the arylthioacetic acid derivative VI by treatment with bromoacetic acid under basic conditions (e.g. aqueous sodium or potassium hydroxide). The reaction temperature for this step is typically between 20° C. and 100° C. Following acidification of the reaction mixture, the product VI is typically isolated by crystallization or, if necessary, it can be purified by chromatography.

Arylthioacetic acid VI is then coupled with a suitable cephem intermediate having a 3–substituent leaving group. For example, the leaving group may be acetoxy or halo. In the preferred embodiment illustrated by the reaction scheme, the cephem intermediate is the 3-chloro cephem V, but other suitable cephem intermediates with equivalent leaving groups at the 3-position could also be employed. The cephem intermediate V may be acylated with VI or a reactive derivative thereof by conventional acylation procedures well-known in the cephalosporin art to give N-acylated intermediate IV. In addition to using the free arylthioacetic acid, e.g. with a suitable condensing agent such as dicyclohexylcarbodiimide, acylating agent VI may also be employed in the form of equivalent acylating derivatives such as an acid anhydride, mixed anhydride, activated ester, or acid halide. The cephem intermediate preferably has the carboxyl group protected by a conventional carboxyl-protecting group which can be readily removed. Examples of such protecting groups are discussed above and include benzyl, 4-nitrobenzyl, 4-methoxybenzyl, diphenylmethyl, allyl, and the like. Other examples of suitable protecting groups are disclosed in *Protective Groups in Organic Synthesis*, Theodora W. Greene (John Wiley & Sons, 1981), Chapter 5. In one embodiment, intermediate V may be acylated with acid VI in the presence of dicyclohexylcarbodiimide and in an inert solvent such as tetrahydrofuran or dichloromethane. The reaction temperature is typically between −20° C. and 50° C. Upon completion of the reaction, insoluble material is removed by filtration, the filtrate is concentrated, and the residue is treated with a relatively non-polar solvent such as diethyl ether or ethyl acetate resulting in precipitation of the desired product. Alternatively, acid VI may be converted to the corresponding acid chloride, for example by treatment with thionyl chloride with or without a solvent such as dichloromethane, followed by coupling with cephem amine V in the presence of a base such as triethylamine or N-methylmorpholine to give intermediate IV. Cephem IV is typically isolated after aqueous work-up and evaporation of volatile solvents followed by trituration of the compound with a relatively non-polar solvent such as diethyl ether or ethyl acetate. This intermediate may be used in the next reaction step as the X=chloride derivative, or can be converted to the X=bromide or X=iodide derivative by treatment with the appropriate metal halide in a solvent such as acetone.

To prepare quaternary cephem X, intermediate IV is deprotected under acidic conditions, followed by reaction of the resulting intermediate IV' with a thiopyridone derivative III. For example, when R is diphenylmethyl or 4-methoxybenzyl, cephem acid IV' is obtained upon treatment of IV with trifluoroacetic acid neat or in an inert solvent such as methylene chloride. A reagent such as anisole may also be employed to scavenge the liberated ester protecting group. The reaction temperature is usually at or below room temperature. The deprotection may also be carried out by treatment with other protic acids such as hydrochloric acid in a solvent such as methanol. The final product is typically isolated by precipitation or crystallization. Reaction of IV' with a thiopyridone derivative III in a solvent such as dimethylformamide, dimethyl sulfoxide, ethanol, methanol, or other appropriate solvents at a temperature between −20° C. and 100° C. affords target quaternary cephem I. The final product is isolated as described above. Thiopyridones III are typically prepared according to a method analogous to that described in T. Takahashi et al., European Patent Application No. 209751 and in I.E. El-Kholy et al., J. Heterocyclic Chem. Vol. 11, p. 487 (1974). This procedure entails reaction of 4-thiopyrone (European Patent No. 209751) with an appropriate primary amine in a solvent such as aqueous methanol or ethanol at a temperature ranging between 0° C. and 78° C. The primary amine may be in the form of a zwitterion in examples where there is a free acid group present in the molecule. In these cases, a base such as sodium hydroxide, sodium bicarbonate, or pyridine is added to form the free amine in situ. The product may be isolated as its sodium salt by evaporation of volatile solvents, followed by trituration with a solvent such as diethyl ether or ethyl acetate. Alternatively, the reaction mixture may be acidified and extracted with an organic solvent to afford the product as the free carboxylic acid. If the carboxylate group is protected as an ester, the amine may be free or present as an acid salt. In the latter case, a base such as sodium hydroxide, sodium bicarbonate, or pyridine is added to form the free amine in situ. The product is typically isolated by precipitation or by reversed phase column chromatography following removal of volatile solvents.

It will be understood that where the substituent groups used in the above reactions contain certain reaction-sensitive functional groups such as amino or carboxylate groups which might result in undesirable side-reactions, such groups may be protected by conventional protecting groups known to those skilled in the art.

For example, thiopyridone intermediates of formula III may have an amine functional group protected as the t-butyloxycarbamate. Suitable protecting groups and methods for their removal are illustrated, for example, in *Protective Groups in Organic Synthesis*, Theodora W. Greene (John Wiley & Sons, 1991). It is intended that such "protected" intermediates and end-products are included within the scope of the present disclosure and claims.

The desired end-product of formula I may be recovered either as the zwitterion or in the form of a pharmaceutically acceptable acid addition salt, e.g. by addition of the appropriate acid such as HCl, HI or methanesulfonic acid to the zwitterion.

It will be appreciated that certain products within the scope of formula I may have a C-3 substituent group which can result in formation of optical isomers. It is intended that the present invention include within its scope all such optical isomers as well as epimeric mixtures thereof, i.e. R- or S- or racemic forms.

In Vitro Activity

Samples of the compounds prepared below in Examples 1–10 after solution in water and dilution with Nutrient Broth were found to exhibit the following Minimum Inhibitory Concentrations (MIC) values versus the indicated microorganisms as determined by tube dilution. The MICs were determined using a broth micro dilution assay in accordance with that recommended by the National Committee for Clinical Laboratory Standards (NCCLS). Mueller-Hinton medium was used except for Streptococci which was tested in Todd Hewitt broth. The final bacterial inoculate contained approximately $5 \times 10^5$ cfu/ml and the plates were incubated at 35° C. for 18 hours in ambient air (Streptococci in 5% $CO_2$). The MIC was defined as the lowest drug concentration that prevented visible growth.

| Microorganism | MIC value in ug/ml |
|---|---|
| S. aureus methicillin resistant A27223 | ≦8 |
| S. pneumoniae A9585 | ≦1 |
| S. pyogenes A9604 | ≦1 |
| E. faecalis A20688 | ≦8 |
| S. aureus A95371, penicillinase negative | ≦1 |
| S. aureus A15090, penicillinase positive | ≦1 |
| S. epidermidis A24548 | ≦1 |
| S. epidermidis A25783, methicillin resistant | ≦2 |
| S. hemolyticus A21638 | ≦2 |

In Vivo Activity

The in vivo therapeutic efficacy of the compounds prepared in Examples 1–10 below after intramuscular injection to mice experimentally infected with the representative MRSA strain A27223 was also measured.

The Determination of the Effectiveness of Antimicrobial Agents in *Staphylococcus aureus* Systemic Infection in Mice Organisms: The test organism, MRSA strain A27223 used to generate systemic infection in mice, is grown on two large Brain Heart Infusion Agar plates. On each plate, 0.5 ml of frozen stock culture is plated out. Plates are then incubated for 18 hours at 30° C. The next day each plate is washed with 20 ml of Brain Heart Infusion Broth and then pooled together. A microscopic direct count of microorganism is done using a 1:1000 dilution of plate wash. After a direct count is obtained, the number of organisms per milliliter is calculated. The count is adjusted to the desired amount of inoculum by diluting in 4% hog mucin. The desired challenge (amount of organisms given to mice) is $2.4 \times 10^8$ cfu/0.5 ml/mouse for MRSA strain A27223. The mice are infected intraperitoneally with 0.5 ml of challenge. Ten non-treated infected mice are used as controls.

Mice: Mice used are male ICR mice. The average weight of the animals is from 20 to 26 grams.

Drug preparation and treatment: Compounds are tested at 4 dose levels, (25, 6.25, 1.56, and 0.39 mg/kg) and prepared in 5% cremophor, unless otherwise specified. Vancomycin is used as the control compound, and is dosed at 6.25, 1.56, 0.39, and 0.098 mg/kg. It is prepared in 0.1M phosphate buffer. There are five infected mice per dose level, and they are treated with 0.2 ml of the test compound, preferably by intramuscular injection. Treatment begins 15 minutes and 2 hours post-infection.

Test duration: A $PD_{50}$ (the dose of drug given which protects 50% of mice from mortality) runs for 5 days. During this time, mortality of mice are checked every day and deaths are recorded. The cumulative mortality at each dose level is used to calculate a $PD_{50}$ value for each compound. Surviving mice are sacrificed at the end of day 5 by $CO_2$ inhalation.

Calculation: Actual calculation of $PD_{50}$ is performed with a computer program using the Spearman-Karber procedure.

Results: The in vivo efficacy, expressed as the $PD_{50}$ value, ranged from about 0.8 to 16.5 mg/kg (for certain compounds, more than one test was carried out; the indicated range is for at least one test result when multiple tests were done).

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

h = hour(s)
mol = mole(s)
mmol = mmole(s)
g = gram(s)
THF = tetrahydrofuran
L = liter(s)
mL = milliliter(s)

-continued $Et_2O$ = diethyl ether
EtOAc = ethyl acetate
MeOH = methanol
DMF = dimethylformamide
DABCO = 1,4-Diazabicyclo[2.2.]octane In the following examples, all temperatures are given in degrees Centigrade. Melting points were determined on an electrothermal apparatus and are not corrected. Proton and carbon-13 nuclear magnetic resonance ($^1$H and $^{13}$C NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Infrared spectra were determined on a Perkin-Elmer 1800 FT-IR spectrometer from 4000 cm$^{-1}$ to 400 cm$^{-1}$, calibrated to 1601 cm$^{-1}$ absorption of a polystyrene film, and are reported in reciprocal centimeters (cm$^{-1}$). Mass spectra were recorded on a Kratos MS-50 or a Finnegan 4500 instrument utilizing direct chemical ionization (DCI, isobutene), fast atom bombardment (FAB), or electron ion spray (ESI). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse phase plates and visualized using UV light or iodine vapors. Reversed-phase column chromatography was performed in a glass column using Baker Octadecyl ($C_{18}$), 40 μm.

1-[3-carboxymethyl-[4-(3-sulfoprop-1-yl)morpholin-4-yl]prop-1-yl]-4-[[(6R)-trans-2-carboxy-8-oxo-7-[(2,5-dichloro-4-phenylthio)acetamido]-5-thia-1-azabicyclo[4.2.0]-oct-2-en-3-yl]methylthio] pyridinium Chloride

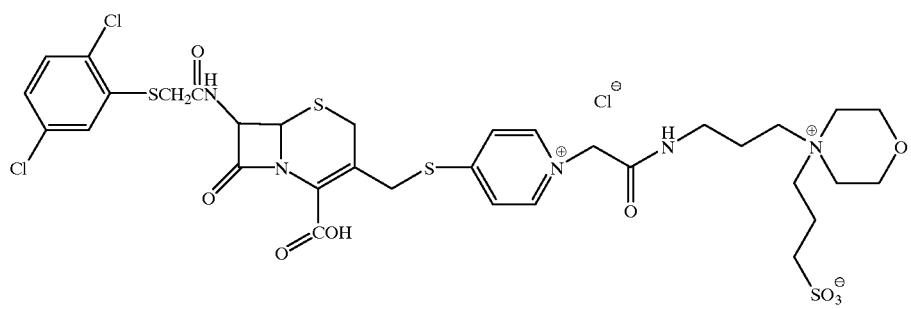

A. 2,5-Dichlorophenylthioacetic Acid

A mixture of 2,5-dichlorothiophenol (10.3 g, 57.5 mmol) and bromoacetic acid (8.03 g, 57.8 mmol) in water (225 mL) was treated with 10 N NaOH (13 mL, 130 mmol) and the mixture was heated at 100° C. for 1 h. The reaction mixture was then cooled to 0° C. and acidified to pH 1 with 6N HCl. The product precipitated and was collected by filtration to give 13.0 g (95% yield) of 2,5-dichlorophenylthioacetic acid as white crystals, m.p. 118° C. $^1$H NMR (300 MHz, CDCl$_3$) δ 3.74 (s, 2H), 7.15 (dd, J=2, 9 Hz, 1 H), 7.32 (d, J=9 Hz, 1 H), 7.36 (d, J=2 Hz, 1 H). Anal. Calcd. for $C_8H_6O_2SCl_2$: C, 40.53; H, 2.55. Found: C, 40.46; H, 2.64.

B. (6R)-trans-3-Chloromethyl-7-[(2,5-dichlorophenyl)thioacetamido]-8-oxo-5-thia-1-azabicyclo[4.2.0]oct-2-ene-2-carboxylate, Diphenylmethyl Ester Method a A solution of 2,5-dichlorophenylthioacetic acid (13.0 g, 54.9 mmol) in methylene chloride (55 mL) and thionyl chloride (10 mL, 137 mmol) was heated at reflux for 3 h. The reaction mixture was allowed to cool to room temperature and was concentrated in vacuo. The residue was evaporated two times from toluene to give 14 g of 2,5-dichlorophenylthioacetyl chloride (100% yield) as a slightly colored product which was used in the next step without purification. $^1$H NMR (300 MHz, CDCl$_3$) δ 4.13 (s, 2 H), 7.22 (dd, J=2, 9 Hz, 1 H), 7.35 (d, J=9 Hz, 1 H), 7.39 (d, J=2 Hz, 1 H).

(6R)-trans-3-Chloromethyl-7-amino-8-oxo-5-thia-1-azabicyclo-[4.2.0]oct-2-ene-2-carboxylate, diphenylmethyl ester, HCl salt was stirred in a biphasic mixture of EtOAc and saturated NaHCO$_3$ for 0.5 h. The layers were separated, and the organic solution was dried over anhydrous MgSO$_4$, filtered, and concentrated to dryness. The free base (9.15 g, 22.0 mmol) was dissolved in THF (200 mL), cooled to 0° C., and treated with N-methylmorpholine (3.34 g, 33.0 mmol) and 2,5-dichlorophenylthioacetyl chloride (6.75 g, 26.4 mmol). The reaction mixture was stirred for 1 h at 0° C., diluted with EtOAc (1000 mL) and washed with water (1000 mL) and brine (100 mL). The organic solution was then dried (MgSO$_4$) and the solvents were evaporated in vacuo. The residue was stirred with ether (100 mL). The product solidified and was collected by filtration to give 12.0 g (86% yield) of (6R)-trans-3-chloromethyl-7-[(2,5-dichlorophenyl)-thioacetamido]-8-oxo-5-thia-1-azabicyclo[4.2.0]oct-2-ene-2-carboxylate, diphenylmethyl ester, m.p. 120° C. $^1$H NMR (300 MHz, CDCl$_3$) δ 3.43 (d, J=18 Hz, 1 H), 3.59 (d, J=18 Hz, 1 H), 3.69 (d, J=17 Hz, 1 H), 3.79 (d, J=17 Hz, 1 H), 4.36 (d, J=12 Hz, 1 H), 4.41 (d, J=12 Hz, 1 H), 4.98 (d, J=5 Hz, 1 H), 5.81 (dd, J=5, 9 Hz, 1 H), 6.98 (s, 1 H), 7.14–7.44 (m, 14 H). Anal. Calcd for $C_{29}H_{23}N_2O_4S_2Cl_3$: C, 54.94; H, 3.66; N, 4.42. Found: C, 55.18; H, 3.84; N, 4.62.

Method b (6R)-trans-3-Chloromethyl-7-amino-8-oxo-5-thia-1-azabicyclo[4.2.0]oct-2-ene-2-carboxylate, diphenylmethyl ester, HCl salt (Otsuka, 248 g, 0.55 mol) was treated with NaHCO$_3$ (56 g, 0.66 mol) in water (1.6 L) at 0° C. The mixture was stirred at 0° C. for 0.5 h and then CH$_2$Cl$_2$ (1.5 L) was added. The biphasic mixture was filtered through Celite and the Celite pad was washed with CH$_2$Cl$_2$ (2 L total). The layers were separated and the organic solution was dried over anhydrous MgSO$_4$, filtered, and concentrated to a volume of ca. 2 L. The free amine solution was then added to a mixture of 2,5-dichlorothiophenylacetic acid (130 g, 0.55 mol) and dicyclohexylcarbodiimide (144 g, 0.70 mol) in THF (1 L) at room temperature. The reaction mixture was stirred for 2.5 h and then was filtered through Celite, washing the Celite pad with several portions of acetone. The filtrate was concentrated in vacuo to give a solid mass. The solid was slurried in Et$_2$O and then collected by filtration, washing the solid with several portions of Et$_2$O. The solid was dried under high vacuum over P$_2$O$_5$ to give 268 g (77% yield) of (6R)-trans-3-chloromethyl-7-[(2,5-dichlorophenyl)thioacetamido]-8-oxo-5-thia-1-azabicyclo[4.2.0]oct-2-ene-2-carboxylate, diphenylmethyl ester (see above for analytical data).

C. (6R)-trans-3-Chloromethyl-7-[(2,5-dichlorophenyl)-thioacetamido]-8]-oxo-5-thia-1-azabicyclo[4.2.0]oct-2-ene-2-carboxylic acid A slurry of (6R)-trans-3-chloromethyl-7-[(2,5-dichlorophenyl)-thioacetamido]-8-oxo-5-thia-1-azabicyclo[4.2.0]oct-2-ene-2-carboxylate, diphenylmethyl ester (10.0 g, 15.8 mmol) in CH$_2$Cl$_2$ (200 mL) at 0° C. was treated with anisole (24 mL) and then trifluoroacetic acid (80 mL). The resulting solution was stirred for 1 h at 0° C. and then concentrated under reduced pressure. The residue was stirred with Et$_2$O, and the resulting solid was collected by filtration to give 5.20 g of (6R)-trans-3-chloromethyl-7-[(2,5-dichlorophenyl)-thioacetamido]-8-oxo-5-thia-1-azabicyclo[4.2.0]oct-2-ene-2-carboxylic acid as a white solid (70% yield), m.p. 125° C. $^1$H NMR (300 MHz, DMSO-d$_6$) δ 3.51 (d, J=18 Hz, 1 H), 3.70 (d, J=18 Hz, 1 H), 3.91 (s, 2 H), 4.52 (d, J=11 Hz, 1 H), 4.58 (d, J=11 Hz, 1 H), 5.13 (d, J=5 Hz, 1 H), 5.70 (dd, J=5, 8 Hz, 1 H), 7.24 (dd, J=2, 8 Hz, 1 H), 7.47 (dd, J=2, 8 Hz, 2 H), 9.28 (d, J=8 Hz, 1 H).

D. 1-[[3-[4-(3-sulfoprop-1-yl)-4-morpholino-]prop-1-yl-aminolcarbonyl]methyl]-4-[[(6R)-trans-2-carboxy-8-oxo-7-[(2,5-dichlorophenylthio)-acetamido]-5-thia-1-azabicyclo[4.2.0]-oct-2-en-3-yl]methylthio]pyridinium chloride 1. Preparation of N-[3-carboxymethyl-[4-(3-sulfoprop-1-yl)-4-morpholino-]prop-1-yl-amino]carbonyl]methyl]] thiopyridone A solution of amino acetamidopropyl morpholino propane sulphobetaine (1.3g, 4 mmol) in MeOH (20 mL) was treated with N-[3-carboxymethyl-[4-(3-sulfoprop-1-yl) morpholin-4-yl]prop-1-yl] (0.5 g, 4.4 mmol) in EtOH (5 mL). The mixture was stirred at room temperature overnight. The MeOH was removed under vacuum, and the residue was triturated with acetone in order to remove excess amount of thiopyrone. The crude product was subjected to a C-18 column chromatography, and eluted with H$_2$O. N-[3-carboxymethyl-[4-(3-sulfoprop-1-yl)morpholin-4-yl]prop-1-yl] N-[3-carboxy methyl-[4-(3-sulfoprop-1-yl)-4-morpholino-]prop-1-yl-amino]carbonyl]methyl]] thiopyridone was obtained, after lyophilization, as a yellow hygroscopic solid (0.31g, 19%). $^1$H NMR (DMSO) δ 8.44 (t, 1H, J=5 Hz), 7.52 (d, 2H, J=7 Hz), 7.12 (d, 2H, J=7 Hz), 4.79 (s, 2H) 3.89–3.71 (m, 4H), 3.62–2.57 (m, 2H), 3.39–3.29 (m, 4H), 3.20–3.12 (m, 2H), 2.53–2.45 (m, 4H), 2.05–1.82 (m, 4H); MS (ESI) 417 (M$^+$).

2. Preparation of 1-[3-carboxymethyl-[N-[3-carboxymethyl-[4-(3-sulfoprop-1-yl)-4-morpholino-]prop-1-yl-amino]carbonyl]methyl]4-[[(6R)-trans-2-carboxy-8-oxo-7-[(2,5-dichlorophenylthio)-acetamido]5-thia-1-azabicyclo[4.2.0]-oct-2-en-3-yl]methylthio]pyridinium chloride To a solution of N-[3-carboxymethyl-[4-(3-sulfoprop-1-yl)-4-morpholino-]prop-1-yl-amino]carbonyl]methyl]]

thiopyridone (0.3 g, 0.72 mmol) in DMF (7 mL) was added 6R)-trans-3-Chloromethyl-7-[(2,5-dichlorophenyl)-thioaceta-mido]-8-oxo-5-thia-1-azabicyclo[4.2.0]oct-2-ene-2-carboxylic acid (0.36 g, 0.76 mmol) in one portion. The mixture was stirred at room temperature for 4 hrs. The DMF was removed in vacuo, and the residue was triturated three times with acetone. 1-[3-carboxymethyl-[4-(3-sulfoprop-1-yl)-4-morpholino-]prop-1-yl-amino]carbonyl]methyl]-4-[[(6R)-trans-2-carboxy-8-oxo-7-[(2,5-dichlorophenylthio)-acetamido]-5-thia-1-azabicyclo [4.2.0]-oct-2-en-3-yl] methylthio]pyridinium chloride was obtained as a tan solid (0.29 g, 48%). $^1$H NMR (DMSO) δ 9.23 (d, 1H, J=8 Hz), 8.91 (t, 1H, J=5 Hz), 8.64 (d, 2H, J=6 Hz), 8.25 (d, 2H, J=6 Hz), 7.47 (m, 2H), 7.24 (dd, 1H, J=2,8 Hz), 5.54 (dd, 1H, J=5, 8 Hz), 5.33 (s, 2H), 5.03 (d, 1H, J=5 Hz), 4.59 (d, 1H, J=13 Hz), 4.34 (d, 1H, J=13 Hz), 3.90 (br s, 4H), 3.70–3.50 (m, 2H), 3.45–3.20 (m, 10H), 2.60–2.45 (m, 4H), 2.05–1.85 (m, 4H); IR (KBr): 3432 (br), 3057, 1770, 1678, 1632, 1563, 1374. 1094 (br) cm$^{-1}$; MS (ESI) 847 (M$^+$).

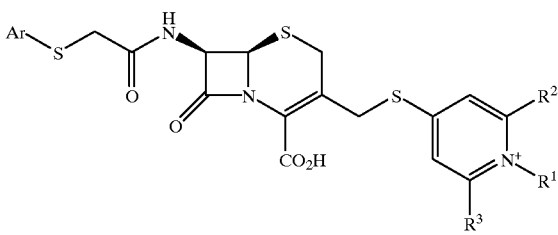

| Example No. | Ar | R$^1$ | R$^2$ | R$^3$ |
|---|---|---|---|---|
| 1 | 2,5-diClPh | [structure with amide, propyl, morpholino-N+, propyl-SO$_3$H] | H | H |
| 2 | 2,5-diClPh | [structure with amide, propyl, N+(CH$_3$)$_2$, CH$_2$CO$_2$H] | H | H |
| 3 | 2,5-diClPh | [structure with butyl, morpholino-N+, CH$_2$CO$_2$H] | H | H |
| 4 | 2,5-diClPh | [structure with butyl, morpholino-N+, CH$_2$CO$_2$H] | CH$_3$ | CH$_3$ |
| 5 | 2,5-diClPh | [structure with butyl, morpholino-N+, propyl-SO$_3$H] | H | H |
| 6 | 2,5-diClPh | [structure with propyl, N+(CH$_3$)$_2$, propyl-SO$_3$H] | H | H |

-continued

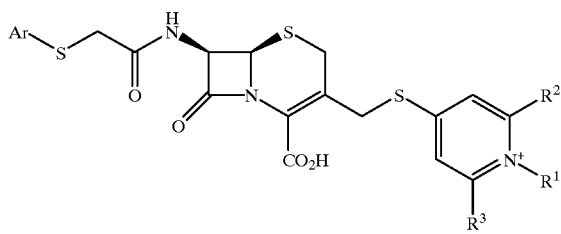

| Example No. | Ar | R¹ | R² | R³ |
|---|---|---|---|---|
| 7 | 2,5-diClPh | (piperidinium with propylsulfonic acid and 4-OH) | H | H |
| 8 | 2,5-diClPh | (pyridoxine-derived N-Me pyridinium) | H | H |
| 9 | 2,5-diClPh | (2-methylimidazolium with CH₂CO₂H) | H | H |
| 10 | 2,5-diClPh | (dimethyl(tetrazol-5-ylmethyl)ammonium) | H | H |

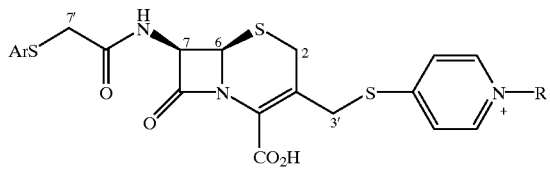

| Compd. of Ex. No. | H-2 | H-6 | H-7 | H-3' | H-7' | NH | ArH | S—PyrH | R | Isolated Form | MS Data |
|---|---|---|---|---|---|---|---|---|---|---|---|
| 1 | 3.70–3.50(m) | 5.03(d, J=5) | 5.54(dd, J=5,8) | 4.59 (d, J=13) 4.34 (d, J=13) | 3.90(s) | 9.23(d, J=8) | 7.47–7.44(m) 7.24(dd, J=2,8) | 8.64(d, J=6) 8.25(d, J=6) | 8.91(t, J=5) 5.33(s) 3.90(br, s) 3.45–3.20(m) 2.60–2.45(m) 2.05–1.85(m) | HCl | M⁺ = 847 |
| 2 | 3.42(d, J=18) 3.14(d, J=18) Overlaps w/R | 4.98(d, J=5) | 5.47(dd, J=5,8) | 4.62(d, J=14) 4.38(d, J=14) | 3.90(s) | 9.30(d, J=8) | 7.42–7.46(m) 7.24–7.20(m) | 8.72(d, J=7) 8.30(d, J=7) | 8.99(m) 5.26(s) 3.59(s) 3.58–3.13(m) 3.07(s) 1.79(m) | Di-bromide | M⁺ = 742 |
| 3 | 3.71(d, J=18) 3.47(d, J=18) | 5.07(d, J=5) | 5.63(dd, J=5,8) | 4.49(d, J=13) | 3.92(s) | 9.31(d, J=8) | 7.48–7.44(m) 7.25(dd, J=2,8) | 8.79(d, J=6) | 4.61–4.41(m) 3.90(s) | HCl/ TFA | M⁺ = 728 |

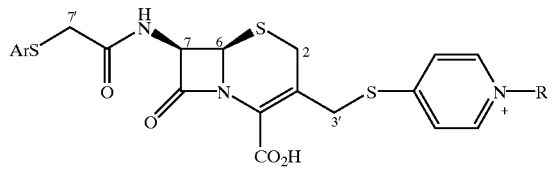

| Compd. of Ex. No. | H-2 | H-6 | H-7 | H-3' | H-7' | NH | ArH | S—PyrH | R | Isolated Form | MS Data |
|---|---|---|---|---|---|---|---|---|---|---|---|
| 4 | 3.79(d, J=18) 3.46(d, J=18) | 5.08(d, J=5) | 5.64(dd, J=5,8) | 4.33(d, J=13) 4.45(dd, J=5,8) 4.31(d, J=13) | 3.92(s) | 9.32(d, J=8) | 7.48–7.44(m) 7.23(dd, J=2,8) | 8.04(d, J=6) 7.85(s) | 3.79–3.44(m) 2.20–2.40(m) 4.47–4.27(m) 4.05–3.58(m) 2.75(s) 2.27–2.07(m) | HCl/ TFA | M+ = 755 |
| 5 | 3.75–3.38(m) | 5.03(d, J=5) | 5.56(dd, J=5,8) | 4.55–4.35(m) | 3.92(s) | 9.28(d, J=8) | 7.48–7.44(m) 7.23(dd, J=2,8) | 8.79(d, J=6) 8.21(d, J=6) | 4.62–4.42(m) 3.75–3.25(m) 2.52–2.32(m) 2.04–1.84(m) | HCl | M+ = 7.91 |
| 6 | 3.13(d, J=17) 3.50(d, J=17) | 4.96(d, J=5) | 5.46(dd, J=5,8) | 4.44(d, J=14) 4.61 9d, J=14) | 3.93(s) | 9.30(d, J=8) | 7.24(dd, J=2,8) 7.45–7.50(m) | 8.44(J=7) 8.90(J=7) | 2.08(m) 2.50(m) 3.60(m) 4.00(m) 4.00(m) | Bis-zwitter-ion | M+ = 735 |
| 7 | 3.75(d, J=18) 3.50(d, J=18) | 5.14(d, J=5) | 5.70(dd, J=5,8) | 4.49–4.29(m) | 3.91(s) | 9.28(d, J=8) | 7.48–7.43(m) 7.26(dd, J=2,8) | 8.79(d, J=7) 8.04(d, J=7) | 4.59–4.39(m) 3.90–3.35(m) 2.49–2.29(m) 2.03–1.83(m) 1.80–1.60(m) | HCl | M+ = 805 |
| 8 | 3.42(d, J=18) 3.35(d, J=18) | 4.95(d, J=5) | 5.45(dd, J=5,8) | 4.68(d, J=13 4.31(d, J=13) | 3.90(s) | 9.25(d, J=8) | 7.50–7.42(m) 7.27–7.24(m) | 8.74(d, J=7) 8.33(d, J=7) | 8.30(s) 4.55(s) 4.20(s) 3.98(s) 2.60(s) | HCl | M+ = 707 |
| 9 | 3.75 (d,J=18Hz) 3.49 (d, J=18Hz) | 5.14 (Obscured) | 5.69 (dd, J=5,8) | 4.40–4.30(m) | 3.91(s) | 9.28(d, J=8) | 7.48(s) 7.44(d, J=7) 7.23(d, J=7) | 8.83(d, J=6) 8.04(d, J=6) | 7.71(s) 7.57(s) 5.14(br s) 4.60–4.50(m) 4.34–4.25(m) 2.60(s) 2.43–2.36(m) | Bis-TFA Salt | M+ = 724 |
| 10 | 3.6 (obscured by H2O peak) | 4.98(d, J=5) | 5.50(dd, J=5,8) | 4.59(d, J=13) 4.47(d, J=13) | 3.93(s) | 9.31(d, J=8) | 7.47–7.44(m) 7.22(t, J=8) | 8.94(d, J=7) 8.34(d, J=7) | 5.15(m) 4.86(s) 3.51(m) 3.10(s) | NaI salt | MH+ = 697 |

We claim:

1. A compound of the formula

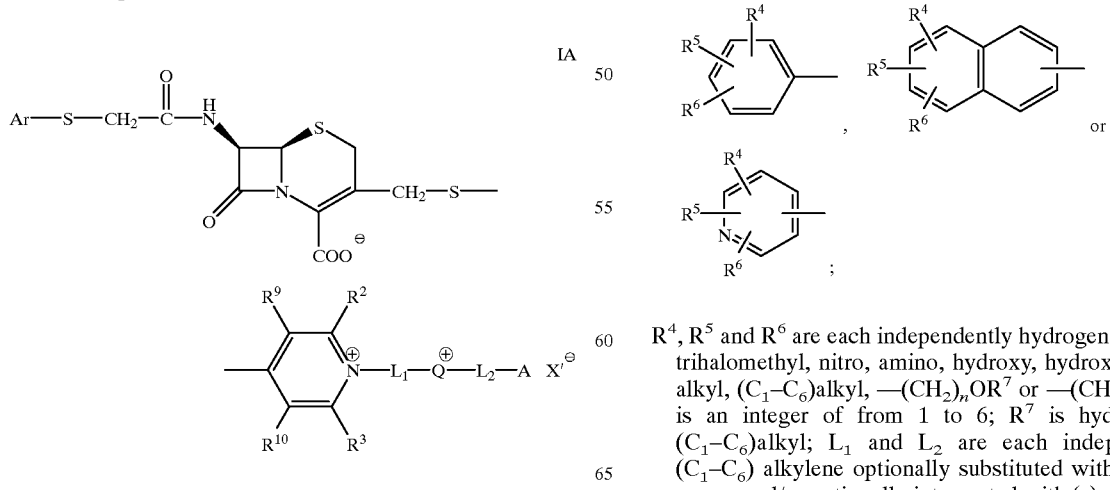

$R^4$, $R^5$ and $R^6$ are each independently hydrogen, halogen, trihalomethyl, nitro, amino, hydroxy, hydroxy($C_1$–$C_6$) alkyl, ($C_1$–$C_6$)alkyl, —$(CH_2)_n OR^7$ or —$(CH_2)_n SR^7$; n is an integer of from 1 to 6; $R^7$ is hydrogen or ($C_1$–$C_6$)alkyl; $L_1$ and $L_2$ are each independently ($C_1$–$C_6$) alkylene optionally substituted with hydroxy or oxo and/or optionally interrupted with (a) a vinylene group, (b) S, (c) O, (d) an arylene or heteroarylene residue, or

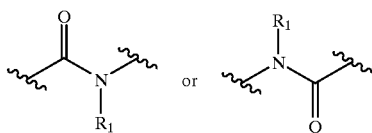

in which $R^1$ is H or $(C_1-C_6)$alkyl; A is $CO_2H$, $PO_3H$, $SO_3H$, tetrazolyl or

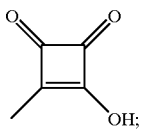

Q is selected from the group consisting of:

(1)

wherein $R^{14}$ and $R^{15}$ are each independently $(C_1-C_{10})$alkyl optionally substituted with OH or $C(O)NH_2$;

(2)

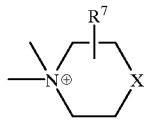

wherein X is $CH_2$, O, S, SO or $SO_2$;

$R^7$ is H, $(C_1-C_6)$ alkyl, $(C_3-C_6)$cycloalkyl, OH, $CONH_2$, aryl or heteroaryl, and can be located anywhere on the ring including X when X is $CH_2$;

(3)

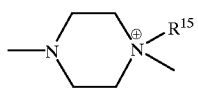

wherein $R^{15}$ is $(C_1-C_6)$alkyl or $(C_3-C_6)$cycloalkyl optionally substituted with OH or $CONH_2$, or $R^5$ is aryl or heteroaryl;

(4)

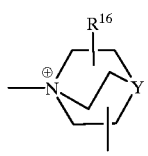

wherein Y is CH or N and $R^{16}$ is as defined above for $R^7$;

(5)

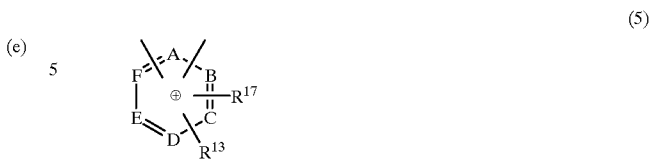

wherein A through F can be CH or N, either 1 or 2 of the non-adjacent ring atoms being N with the remainder being CH, one N being quaternized by attachment to $L_1$, $L_2$, $R^{17}$, or $R^{13}$; $R^{13}$ and $R^{17}$ are as defined above for $R^7$;

(6)

wherein G, H, I, and J are either CH or N, K is either $CH_2$, NH, or S, either 1, 2, or 3 of the ring atoms being nitrogen with the remainder being $CH_2$, exactly one nitrogen being quaternized by $L_1$, $L_2$, or $R^{18}$, and $R^{18}$ is as defined above for $R^7$; $R^2$, $R^3$, $R^9$ and $R^{10}$ are each independently hydrogen, $(C_1-C_{10})$alkyl or $(C_1-C_{10})$alkyl substituted by one or more substituents independently selected from hydroxy and $NR^{11}R^{12}$ in which $R^{11}$ and $R^{12}$ are each independently hydrogen or $(C_1-C_6)$alkyl, and $X'^{\ominus}$ is a pharmaceutically acceptable anion; or a pharmaceutically acceptable salt thereof.

2. A compound of the formula

ID

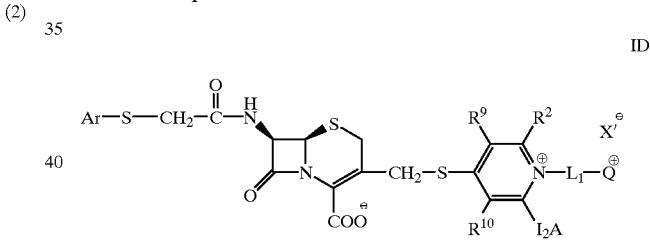

wherein Ar is a group of the formula

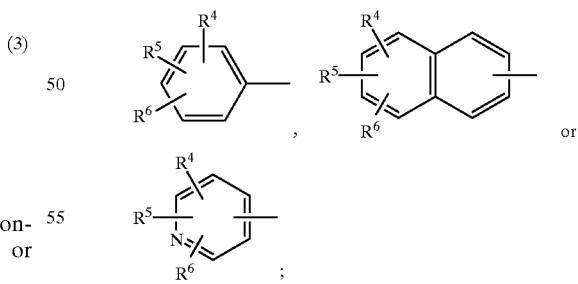

$R^4$, $R^5$ and $R^6$ are each independently hydrogen, halogen, trihalomethyl, nitro, amino, hydroxy, hydroxy$(C_1-C_6)$ alkyl, $(C_1-C_6)$alkyl, $—(CH_2)_nOR^7$ or $—(CH_2)_nSR^7$; n is an integer of from 1 to 6; $R^7$ is hydrogen or $(C_1-C_6)$alkyl; $L_1$ is $(C_1-C_6)$alkylene optionally substituted with hydroxy or oxo and/or optionally interrupted with (a) a vinylene group, (b) S, (c) O, (d) an arylene or heteroarylene residue, or

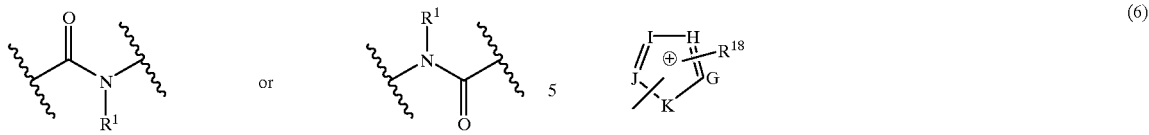

in which R' is H or $(C_1-C_6)$alkyl; Q is selected from the group consisting of:

(1)

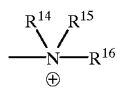

wherein $R^{14}$, $R^{15}$ and $R^{16}$ are each independently $(C_1-C_{10})$ alkyl optionally substituted with OH or $C(O)NH_2$;

(2)

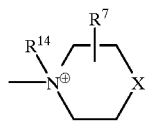

wherein X is $CH_2$, O, S, SO or $SO_2$; $R^7$ is H, $(C_1-C_6)$ alkyl, $(C_3-C_6)$cycloalkyl, OH, $CONH_2$, aryl or heteroaryl and can be located anywhere on the ring including X when X is $CH_2$; and $R^{14}$ is as defined above;

(3)

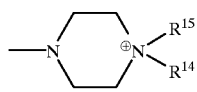

wherein $R^{15}$ is $(C_1-C_6)$alkyl or $(C_3-C_6)$cycloalkyl optionally substituted with OH or $CONH_2$, or $R^{15}$ is aryl or heteroaryl; and $R^{14}$ is as defined above;

(4)

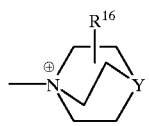

wherein Y is CH or N and $R^{16}$ is as defined above for $R^7$;

(5)

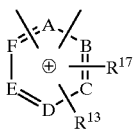

wherein A through F can be CH or N, either 1 or 2 of the non-adjacent ring atoms being N with the remainder being CH, one N being quaternized by attachment to $L_1$, $R^{17}$, or $R^{13}$; $R^{13}$ and $R^{17}$ are as defined for $R^7$;

(6)

wherein G, H, I, and J are either CH or N, K is either $Ch_2$, NH, or S, either 1, 2, or 3 of the ring atoms being nitrogen with the remainder being $CH_2$, one nitrogen being quaternized by $L_1$ or $R^{18}$; and $R^{18}$ is as defined above for $R^7$;

$R^2$, $R^3$, $R^9$ and $R^{10}$ are each independently hydrogen, $(C_1-C_{10})$alkyl or $(C_1-C_{10})$alkyl substituted by one or more substituents independently selected from hydroxy and $NR^{11}R^{12}$ in which $R^{11}$ and $R^{12}$ are each independently hydrogen or $(C_1-C_6)$alkyl, and $X'^{\ominus}$ is a pharmaceutically acceptable anion; or a pharmaceutically acceptable salt thereof.

3. A compound as claimed in claim 1 of the formula

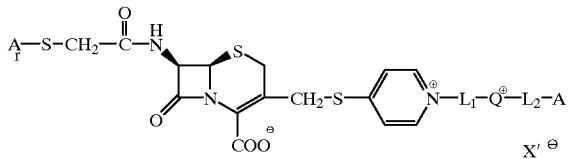

wherein $L_1$ and $L_2$ are $(C_1-C_6)$alkylene, A is either $SO_3H$ or tetrazolyl; and Q is selected from (1)

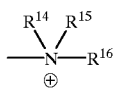

where $R^{14}$ and $R^{15}$ are each independently $(C_1-C_4)$alkyl and (2)

where X is $CH_2$, O, S, SO or $SO_2$.

4. A compound of claim 1, 2 or 3 wherein Ar is

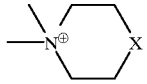

5. A compound of the formula

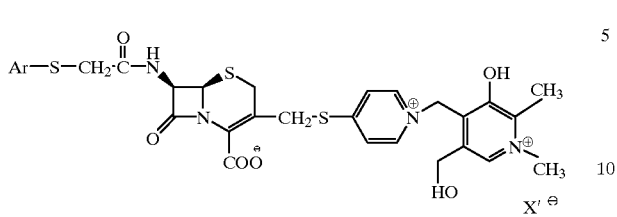

wherein Ar is a group of the formula

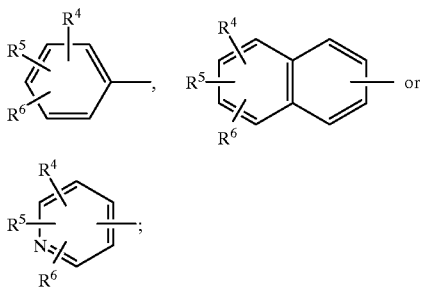

$R^4$, $R^5$ and $R^6$ are each independently hydrogen, halogen, trihalomethyl, nitro, amino, hydroxy, hydroxy($C_1$–$C_6$)alkyl, ($C_1$–$C_6$)alkyl, —$(CH_2)_n OR^7$ or —$(CH_2)_n SR^7$; n is an integer of from 1 to 6;

$R^7$ is hydrogen or ($C_1$–$C_6$)alkyl; and $X'^{\ominus}$ is a pharmaceutically acceptable anion; or a pharmaceutically acceptable salt thereof.

6. A compound of the formula

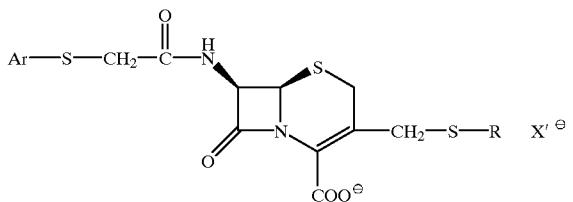

wherein Ar is

in which $R^4$, $R^5$ and $R^6$ are each independently hydrogen, halogen, ($C_1$–$C_6$)alkyl, trifluoromethyl, hydroxy, hydroxy ($C_1$–$C_6$)alkyl or amino;

R is

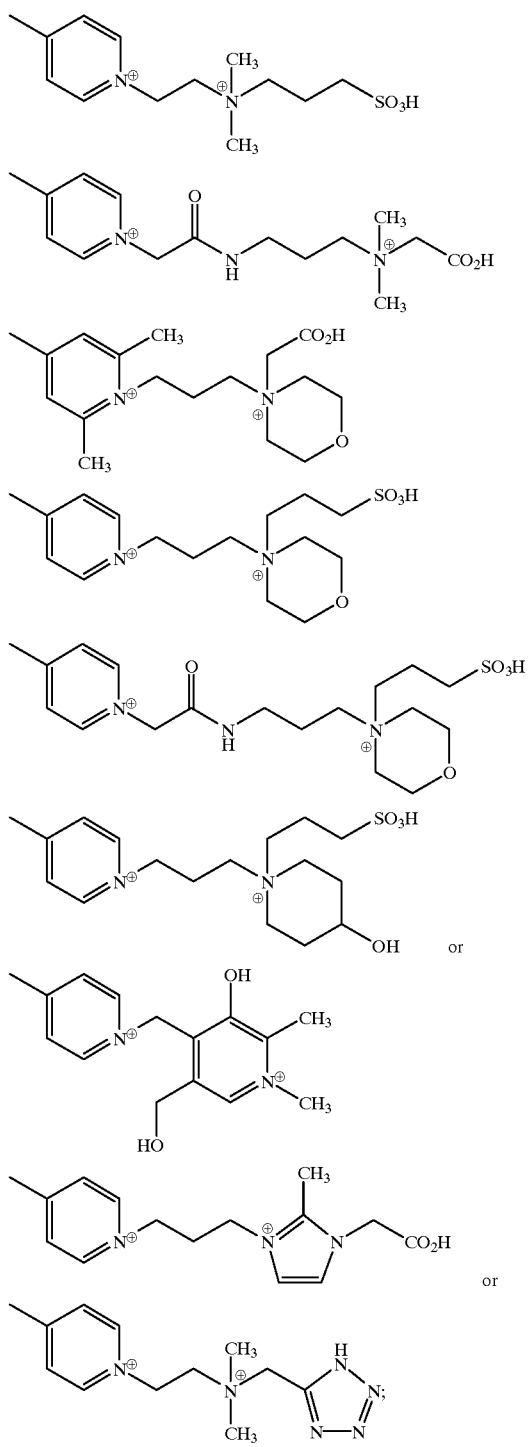

and $X'^{\ominus}$ is a pharmaceutically acceptable anion; or a pharmaceutically acceptable salt thereof.

7. A compound of the formula
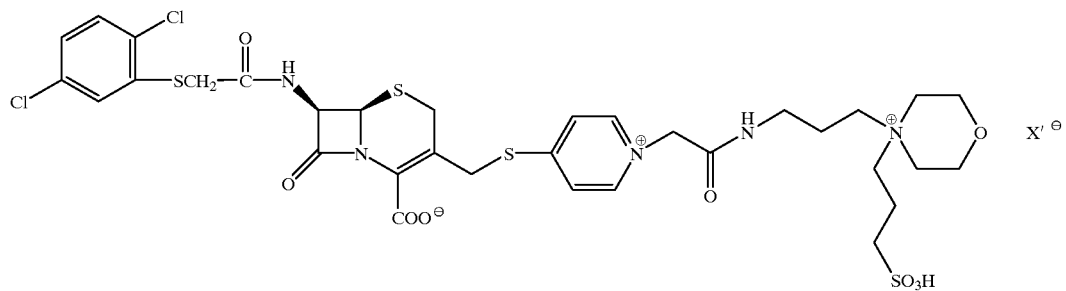
wherein X' is a pharmaceutically acceptable anion.
8. A compound of the formula
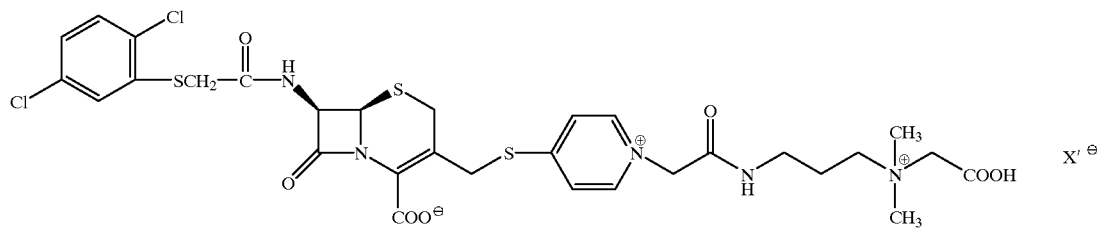
wherein X' is a pharmaceutically acceptable anion.
9. A compound of the formula
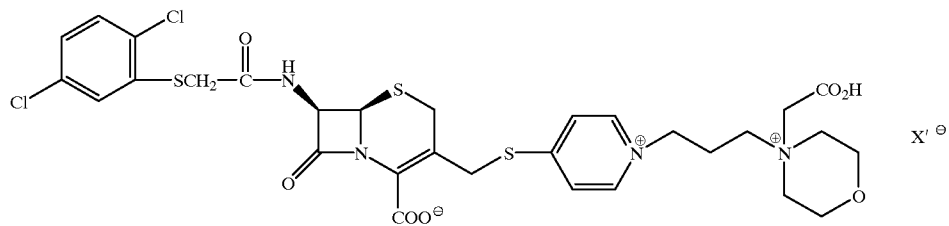
wherein X' is a pharmaceutically acceptable anion.
10. A compound of the formula
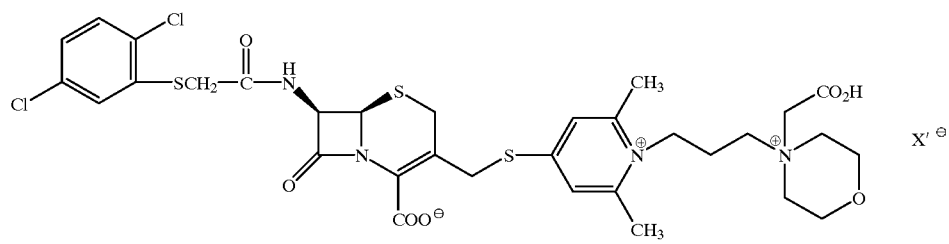
wherein X' is a pharmaceutically acceptable anion.

11. A compound of the formula
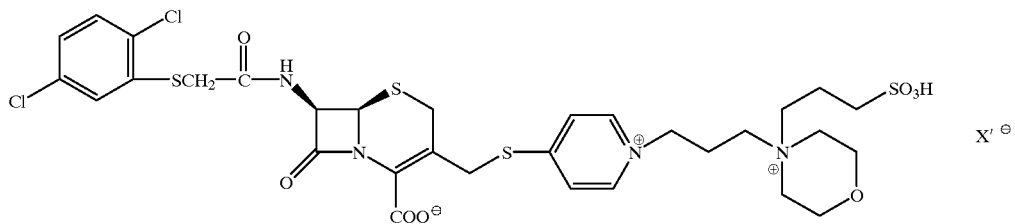
wherein X' is a pharmaceutically acceptable anion.
12. A compound of the formula
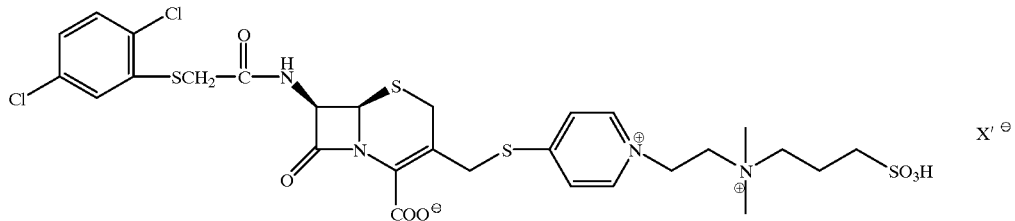
wherein X' is a pharmaceutically acceptable anion.
13. A compound of the formula
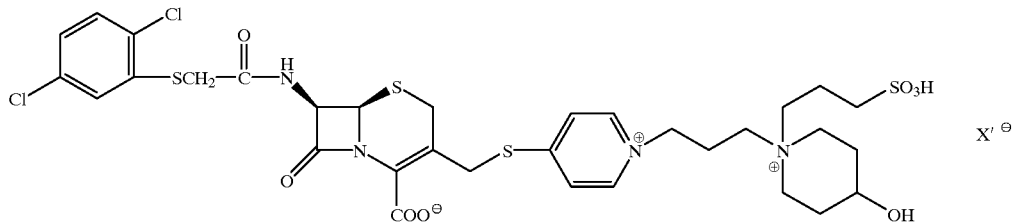
wherein X' is a pharmaceutically acceptable anion.
14. A compound of the formula
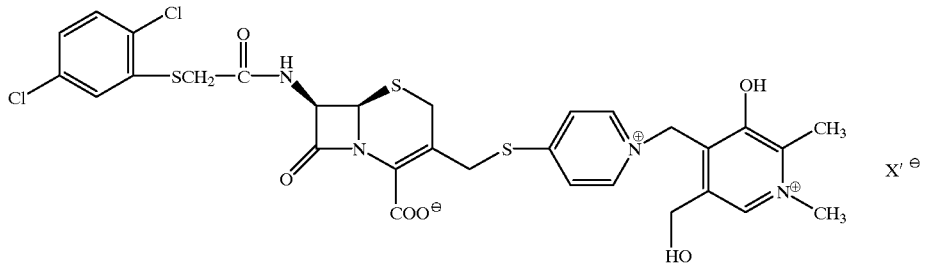
wherein X' is a pharmaceutically acceptable anion.

15. A compound of the formula

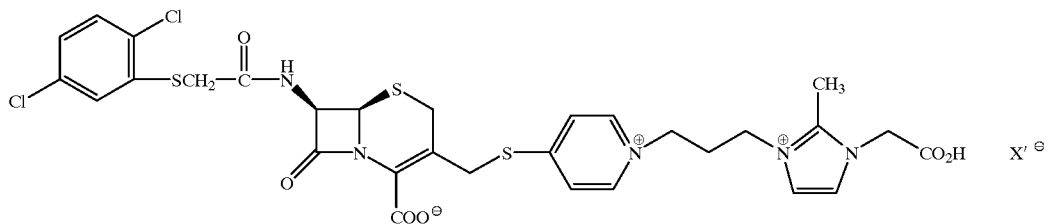

wherein X' is a pharmaceutically acceptable anion.

16. A compound of the formula

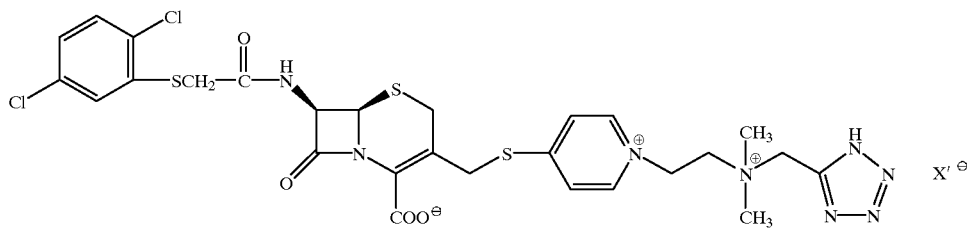

wherein X' is a pharmaceutically acceptable anion.

17. A pharmaceutical composition comprising an effective antibacterial amount of a compound of claim 1 and a pharmaceutically acceptable carrier or excipient.

18. A pharmaceutical composition comprising an effective antibacterial amount of a compound of claim 2 and a pharmaceutically acceptable carrier or excipient.

19. A pharmaceutical composition comprising an effective antibacterial amount of a compound of claim 5 and a pharmaceutically acceptable carrier or excipient.

20. A method of treating a bacterial infection which comprises administering to a host afflicted with such infection an effective antibacterial amount of a compound of claim 1.

21. A method treating a bacterial infection which comprises administering to a host infection an effective antibacterial amount of a compound of claim 2.

22. A method treating a bacterial infection which comprises administering to a host infection an effective antibacterial amount of a compound of claim 5.

* * * * *